United States Patent [19]

Miki et al.

[11] Patent Number: 5,472,669
[45] Date of Patent: Dec. 5, 1995

[54] PRETREATMENT APPARATUS FOR ANALYSIS OF SUGAR

[75] Inventors: Kojiro Miki, Kouga; Takeshi Mori, Kyoto; Hiromi Ohkawa, Joyo; Yumi Hosokawa, Higo; Akihiro Kondo, Muko; Ikunoshin Kato, Uji, all of Japan

[73] Assignees: Horiba, Ltd.; Takara Shuzo Co., Ltd., both of Kyoto, Japan

[21] Appl. No.: 19,593

[22] Filed: Feb. 19, 1993

[30] Foreign Application Priority Data

Feb. 22, 1992 [JP] Japan ................... 4-072627

[51] Int. Cl.$^6$ ................................................. G01N 35/10
[52] U.S. Cl. ...................... 422/63; 422/65; 422/67; 422/68.1; 422/100; 422/104; 436/43; 436/47; 436/48; 436/49; 436/174; 436/179; 436/180
[58] Field of Search .................. 422/63–67, 99, 422/100, 103, 104, 72, 68.1; 436/43, 45, 47, 48, 49, 54, 174, 180, 179

[56] References Cited

U.S. PATENT DOCUMENTS

| | | | |
|---|---|---|---|
| 4,287,155 | 9/1981 | Tersteeg et al. | 422/64 |
| 4,345,843 | 8/1982 | Berglund et al. | 366/219 |
| 4,518,264 | 5/1985 | Nohso | 366/208 |
| 4,535,585 | 8/1985 | Gardos | 53/247 |
| 4,824,641 | 4/1989 | Williams | 422/100 |
| 4,835,707 | 5/1989 | Amano et al. | 364/497 |
| 4,931,256 | 6/1990 | Mack et al. | 422/65 |
| 4,975,533 | 12/1990 | Kondo et al. | 536/55.3 |
| 4,982,553 | 1/1991 | Itoh | 53/246 |
| 5,008,082 | 4/1991 | Shaw | 422/65 |
| 5,018,703 | 4/1992 | Pfost et al. | 422/65 |
| 5,080,864 | 1/1992 | Shaw | 422/62 |
| 5,089,230 | 2/1992 | Kondo et al. | 422/64 |
| 5,200,151 | 4/1993 | Long | 422/100 |
| 5,237,717 | 12/1993 | Marvin | 422/100 |
| 5,324,480 | 6/1994 | Shumate et al. | 422/63 |

FOREIGN PATENT DOCUMENTS

| | | |
|---|---|---|
| 2129254 | 10/1972 | France . |
| 2630216 | 4/1988 | France . |
| 185669 | 6/1989 | Japan . |
| 1141356 | 6/1989 | Japan . |

OTHER PUBLICATIONS

Patent Abstracts of Japan, vol. 11, No. 15, Jan. 16, 1987, JP-A-61 189 457.
"Rovotic Sample Preparation Evaluated for the Immunochemical Determination of Cardiac Isoenzymes", William J. Castellani et al., 6027 Clinical Chemistry, vol. 32, No. 9, Sep. 1986.
"Techniques & Instrumentation in Analytical Chemistry", M. Valcarel et al., vol. 9: Automatic Methods of Analysis, 1988.
Patent Abstracts of Japan, vol. 15, No. 513, Dec. 16, 1991, JP-A003 226 484.
Patent Abstracts of Japan, vol. 15, No. 513, Dec. 26, 1991, JP-A-03 226 485.

*Primary Examiner*—James C. Housel
*Assistant Examiner*—Long V. Le
*Attorney, Agent, or Firm*—Price, Gess & Ubell

[57] ABSTRACT

Pretreatment apparatus and process for analysis of sugar, the apparatus including a mechanical work hand which moves a vial containing a sample to various stations where reagents are added to the vial and where other pretreatment processes are performed on the sample. The pretreatment apparatus automatically controls the movement of the vial from one station to another and the various processes performed at each station, the processes including removal and storage of the vial's cap, addition of reagents into the vial, centrifugation and heating of the sample, and evaporation of excess reagents.

13 Claims, 22 Drawing Sheets

5,472,669

PRETREATMENT APPARATUS FOR ANALYSIS OF SUGAR

BACKGROUND OF THE INVENTION

1. Field of the Invention

The present invention relates to an apparatus and process for conducting a pretreatment of a sample prior to an analysis for the presence of specific sugar molecular chains.

2. Description of Related Art

The analysis of molecular sugar chains in samples of products is frequently conducted in laboratories. There are numerous examples of sugar molecular chains that are analyzed, such as D-glucose, L-fructose, etc. In conducting such an analysis, a pretreatment procedure is utilized to isolate the sugar molecular chains for labeling with fluorescence. This frequently occurs by taking the sample in a sample vial, and with the screw cap of the mouth portion of the sample vial removed. The sample vial is placed in a centrifugal stirrer with a reagent, for example, pyridylamination, which is mixed into the sample vial and stirred. The sample vial is then transferred to a heater and heated. Subsequently, the heated sample vial is transferred to an evaporator, where the excess reagents for pyridylamination are removed. The sample vial, with the reagents being evaporated away, is then returned to the centrifugal stirrer. A reducing reagent is then poured into the sample vial. If the pouring tip is with the sample vial, the tip is replaced prior to adding each reagent to prevent any contamination with the reagent. The reducing agent is then stirred, and the sample vial is again transferred to a heater for heating the sample. The heated sample vial is then returned to the centrifugal stirrer. The pouring tip is again replaced so that a first azeotropic reagent can be poured into the sample vial and stirred to ensure a thorough mixing. The tip can then be replaced again to pour a second azeotropic reagent into the sample vial, again followed by stirring. The sample vial is then transferred to an evaporator to again evaporate the reagents, with the sample vial then again returned to the centrifugal stirrer. Third and fourth reagents can again be poured into the sample vial in the same manner as previously described. The pouring tip is again replaced to accommodate a fifth azeotropic reagent for mixing in the sample vial. Again, the mixture is stirred and then transferred to the evaporator to conduct a further evaporation. The screw cap can be put onto the sample vial to close the mouth portion of the sample vial. The sample vial is then returned to its storing position.

As can be readily determined from the above procedure, a number of the process steps require repetitive removing and mounting of the screw cap onto the sample vial and a repetitive replacement of the reagent-dividing pouring tips with repetitive pouring of reagents in the sample vial and transfers of the sample vial between the centrifugal stirrer, the heater, and the evaporator. These steps are frequently labor intensive and have been manually conducted as part of the pretreatment before analysis for the presence of sugar molecular chains. The manual labor can not only be costly, but errors can occur and the reproduceability of the test procedure can accordingly suffer. Thus, the prior art is still seeking improved procedures and apparatus to provide an efficient pretreatment of samples for determining the contents of sugar molecules and the like.

SUMMARY OF THE INVENTION

The present invention is achieved through the provision of an automatic process and machinery to enable a pretreatment apparatus for use in an analysis of sugars and the like. In accomplishing the present invention, apparatus is provided for storing a portion of reagent-divided pouring tips, reagent-containing vials, and sample vials. A chuck device is capable of contacting and rotating the sample vial. The reagents can be automatically poured into the sample vial from which a cap has been removed. The centrifugal stirrer can be used for weighing the dividedly-poured reagent and stirring the reagent and the sample. A heater is provided for the stirred reagent, along with an evaporator. A mechanical grouping member of a work hand can move across the various work stations in a three-dimensional manner. A pair of guide rails on either side of the work surface support mounting brackets that support a traversely-mounted guide rail that permits the working hand or vice member to move vertically relative to the work surface. By appropriate programming and switch mechanisms, the location of the work hand and the position in which it is to move can be automatically controlled, as known in the art. The sample vials are appropriately positioned in an entrance work station, and the work hand can remove the storage cap through positioning the sample vial in a chucking device. The storage cap can be appropriately stored on a work table designed for that purpose. The sample vial can move to a centrifugal stirrer, where the sample vial is appropriately mounted. A reagent dispensing device can not only be located to dispense reagents into the sample vial, but can also be mounted to other work stations to receive dispensable nozzle tips that can interface with vials of appropriate reagents. A controlled amount of reagent can be introduced into the sample vial. A beater member positioned adjacent the centrifuged apparatus is capable of stirring the solution. An appropriate heater work station and evaporator work station can both heat the mixture and evaporate excess reagents. A cleaning station can appropriately rinse the evacuation line to ensure that contamination will not exist in subsequent processing of samples. Throughout this pretreatment, the work hand of the present invention can be moved from station to station to assist in performing operations that heretofore have been cumbersome and troublesome. These include the removal and mounting of the screw cap from and on the sample vial, the replacement of the nozzle tip for drawing and dispensing reagent solutions, the pouring of the reagents into the sample vial, and the transfer of the sample vial to various work stations. These can all be accomplished in an automatic manner as a result of the configurations of the various apparatuses at the work stations and their compatibility in interfacing with the sample vial, its various closures, and the mechanical work hand.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a pretreatment apparatus and process for analysis of sugar.

Figure 1:
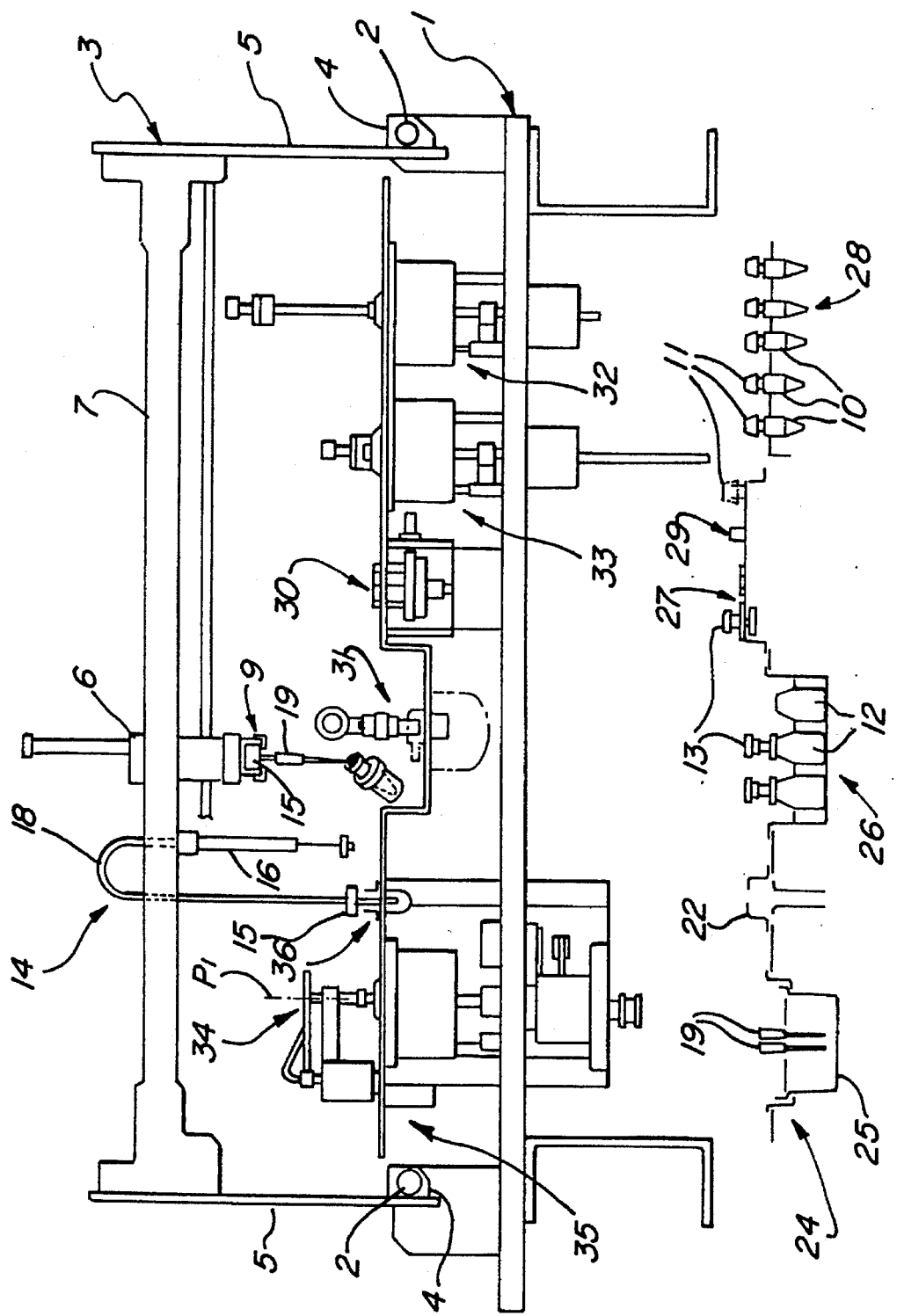
FIG. 1 is a schematic perspective view showing certain main portions of a reagent reacting apparatus, including the relative positions of the various work stations.
Figure 2:
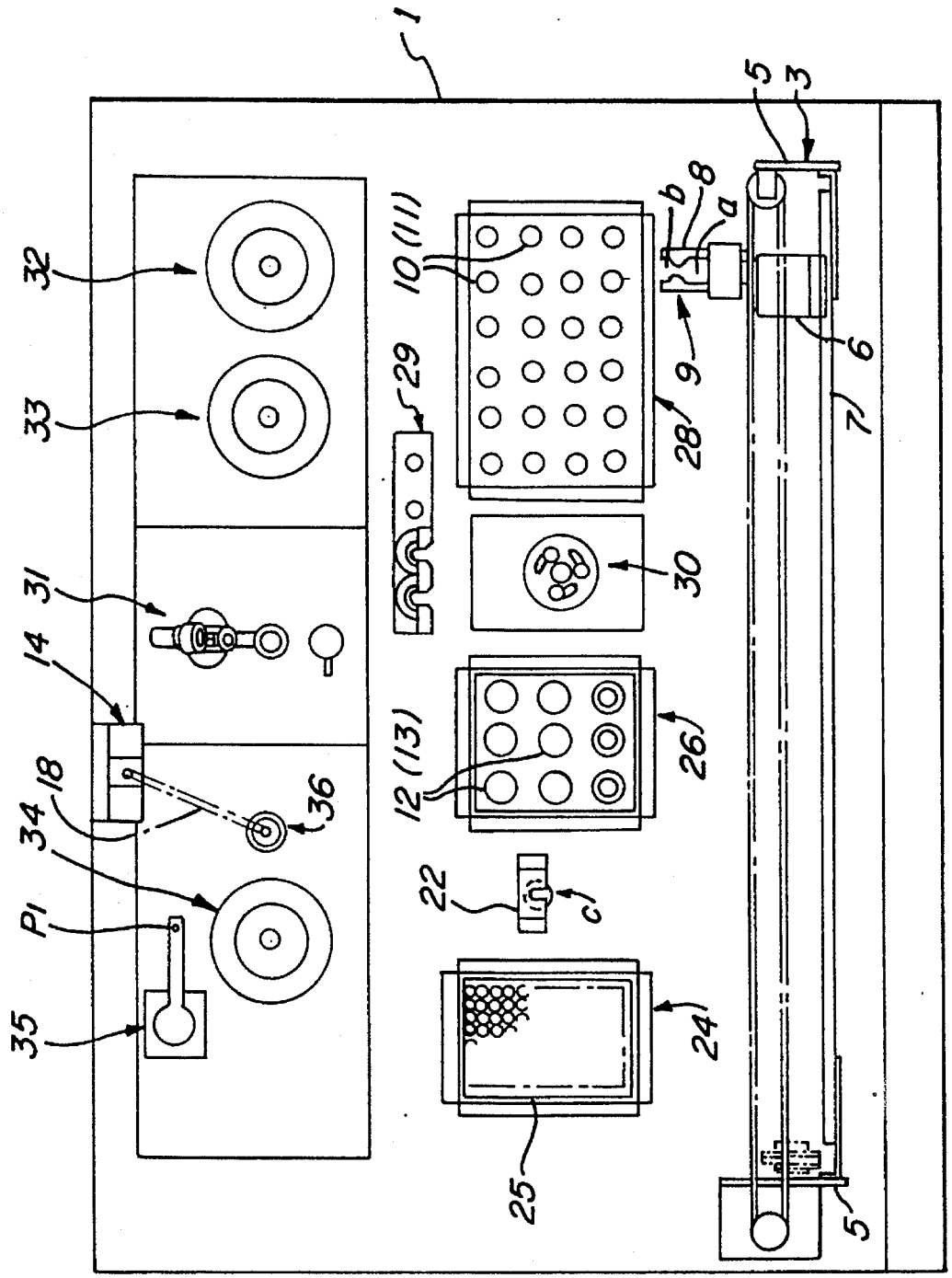
FIG. 2 is a schematic plan view of a location of various work stations on the work surface.
Figure 3:
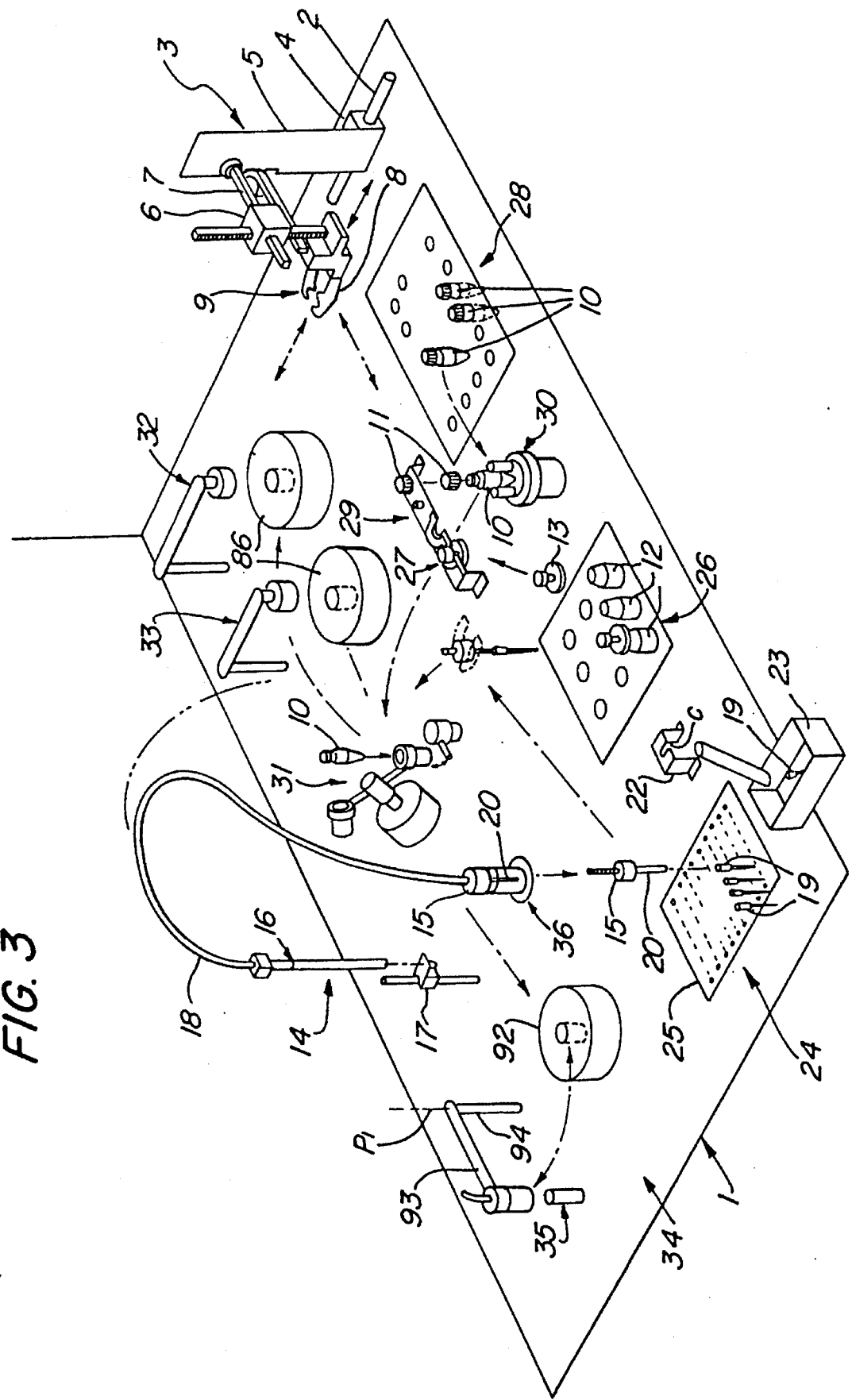
FIG. 3 is a schematic elevated view disclosing the relative positions of various work stations, including repetitive disclosures of elements interfacing with various work stations; for illustrative purposes only.

The preferred embodiments will hereinafter be described with reference to the drawings. FIGS. 1 and 2 are respectively a schematic side view and plan view of the automatic pretreatment apparatus that can be used prior to an analysis of the contents of a sample, such as a sample containing sugar molecules. FIG. 3 is a perspective view illustrating the various relationships of the work stations and possible movements of component parts of the system.

Referring to FIGS. 1–3, the base of the apparatus 1 can support a pair of shafts 2 extending along opposite edges of the base member. Linear bearing members 4 can be journalled on these shafts to support a U-shaped bracket member or frame 3 that can be reciprocally moved back and forth along the shafts 2. Right and left support or leg members 5 mount a horizontal rail member 7 which extends traversely across the apparatus base 1 relative to the shafts 2. A bearing member or slider 6 is reciprocally mounted along the horizontal member 7 and operatively supports a mechanical, vice grip or work hand 9. The work hand 9 includes a pair of relatively movable finger members 8 that can be opened and closed by a solenoid, electrical motor, etc. (not shown). As known in this field, the work hand 9 can be automatically controlled and driven to ascend and descend in the vertical direction as it can be moved in the X and Y directions across the base apparatus 1.

Figure 26:
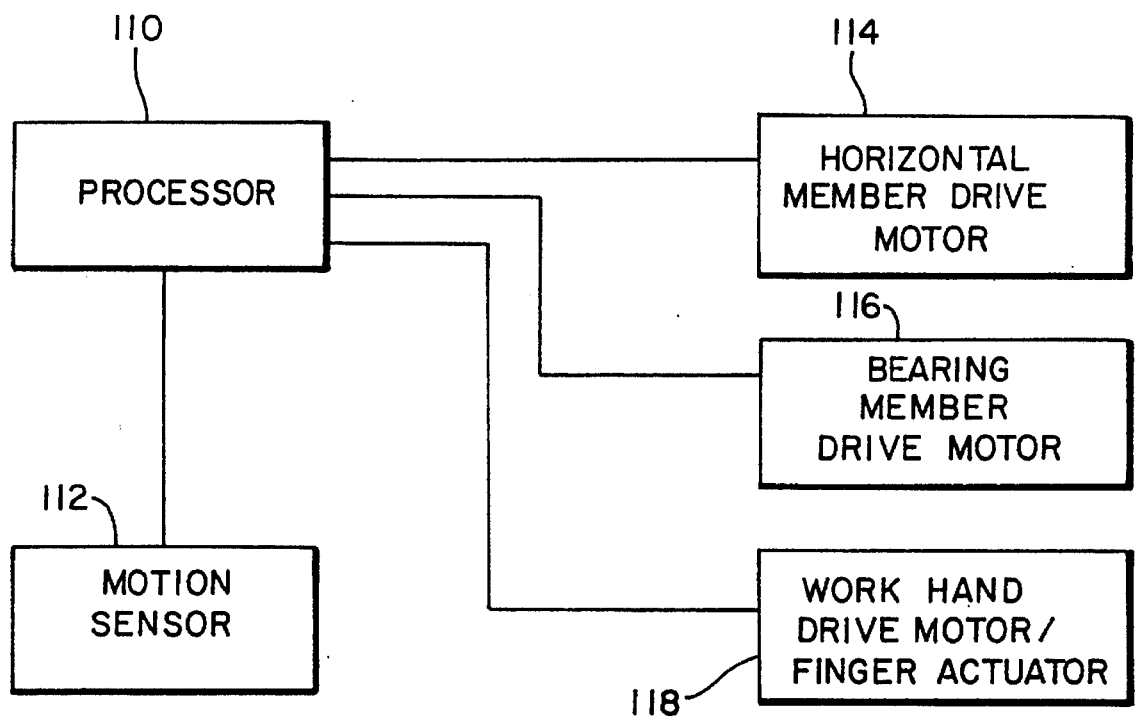
FIG. 26 is a schematic of a control system.

FIG. 26 provides an example of how a processor 110 can be used to automatically control the movement of work hand 9. A motion sensor 112, such as a position sensor, a velocity sensor, or an accelerometer, provides processor 110 with information relating to the movement of work hand 9. Motion sensor 112 may be, but is not necessarily, mechanically attached to work hand 9. The information provided to processor 110 by motion sensor 112 is referenced to a fixed point such as base 1.

Processor 110 controls movement of work hand 9 in the X and Y directions across the base 1 by controlling the movement of bearing member 6 along horizontal member 7, and by controlling the movement of horizontal member 7 and its leg members 5 along shafts 2. FIG. 26 illustrates that processor 110 controls horizontal member drive motor 114 which, in turn, controls movement of horizontal member 7 in the Y direction across the base 1. Similarly, processor 110 sends a signal to bearing member drive motor 116, which controls the movement of bearing member 6 in the X direction across the base 1. Lastly, processor 110 provides an input signal to work hand drive motor/finger actuator 118, which controls vertical movement of work hand 9, and which opens and closes the fingers of work hand 9. Thus, the work hand 9 can address various work stations across the base apparatus 1.

The pretreatment apparatus disclosed herein is particularly advantageous in that it eliminates much of the manual labor inherent in the pretreatment of samples. The time that a technician normally must commit to adding various reagents, stirring vials containing reagents, and centrifuging the sample is made available for other activities because of the automatic nature of the disclosed subject matter. An additional advantage of the apparatus and process for analysis of sugar is that it eliminates the ever-present potential for human error when precise quantities of reagents must be measured and put into a vial. Improved quality control, as well as time savings, are the principal benefits derived from use of the pretreatment apparatus.

Figure 4:
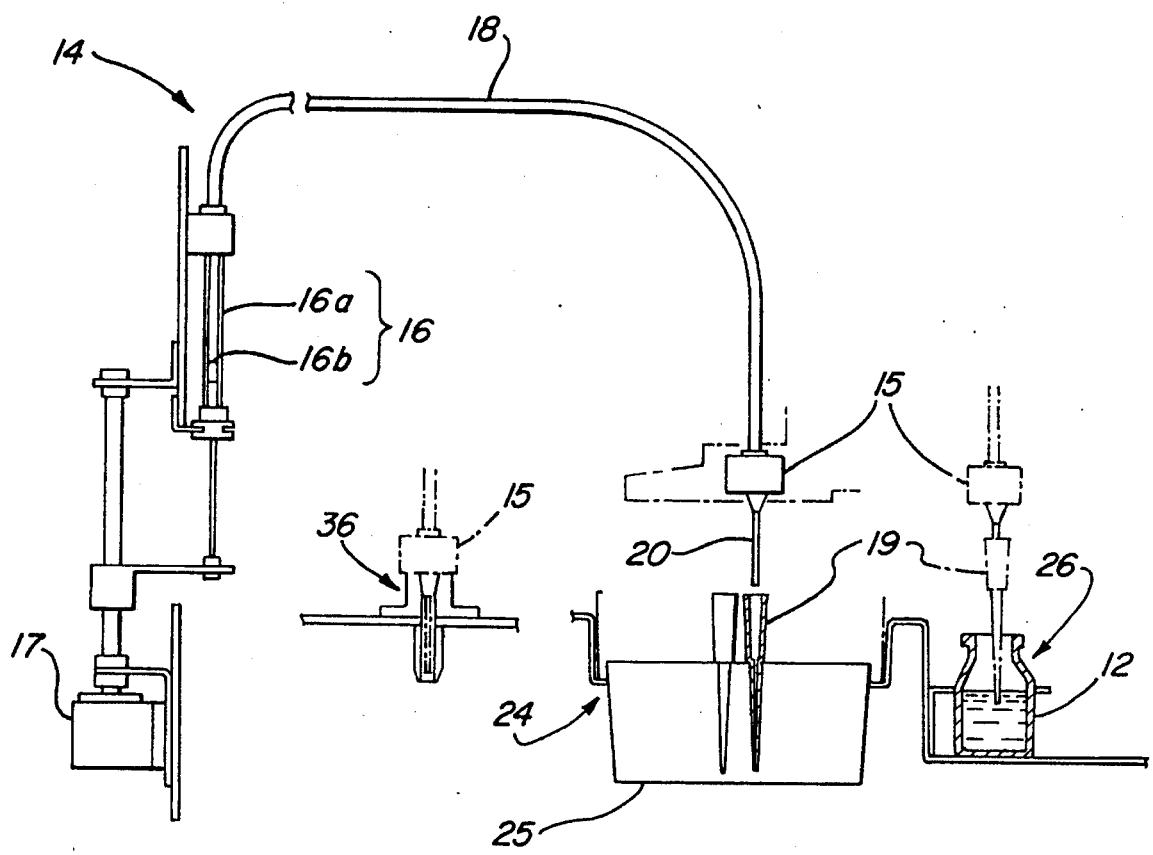
FIG. 4 is an elevated schematic view disclosing a pumping apparatus for dispensing a reagent into a sample vial.
Figure 10:
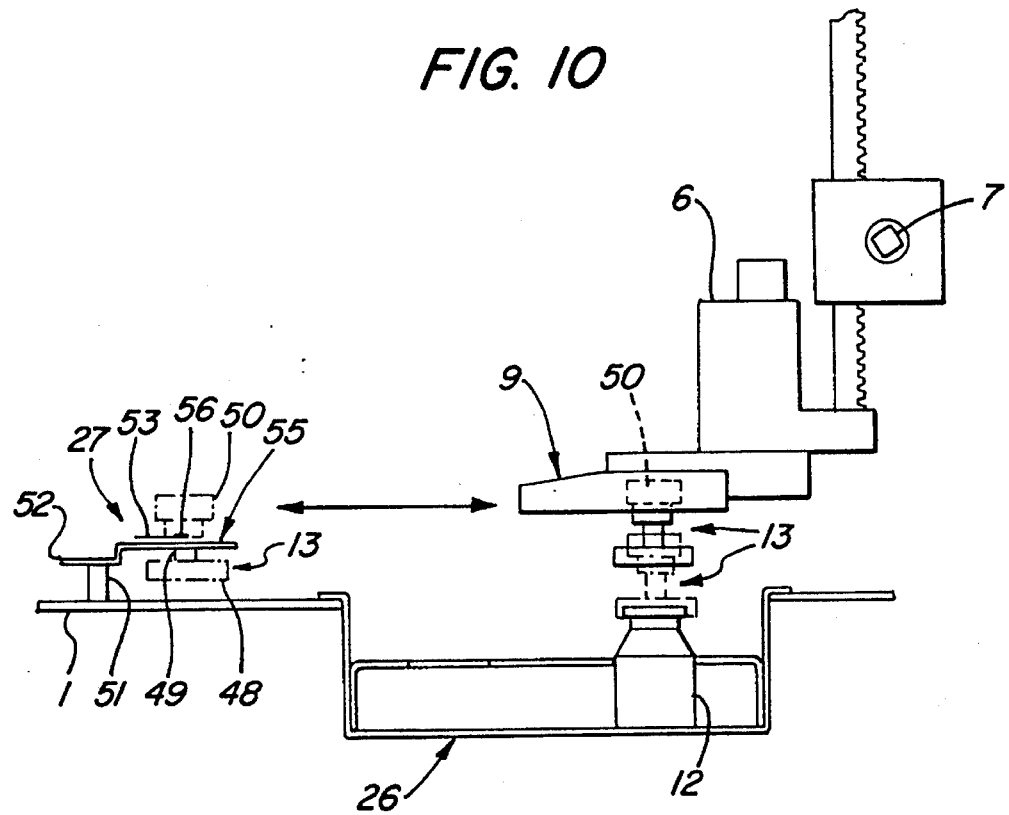
FIG. 10 is a schematic elevated view to illustrate the temporary storage of a vial cover member on a storage table by the mechanical hand.
Figure 11:
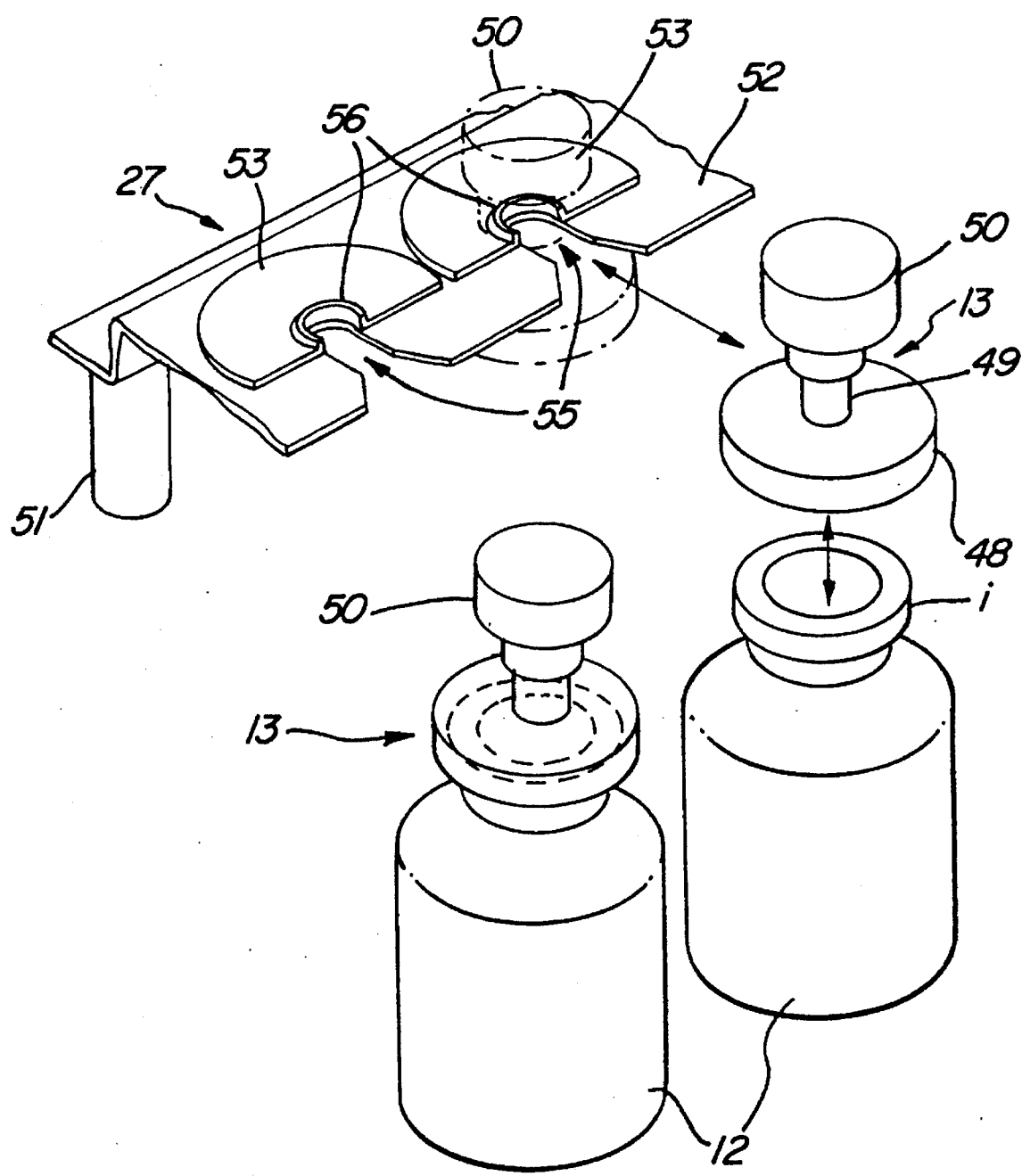
FIG. 11 is a perspective view disclosing the relationship between the reagent-containing vials and the storage table and vial covers.
Figure 14:
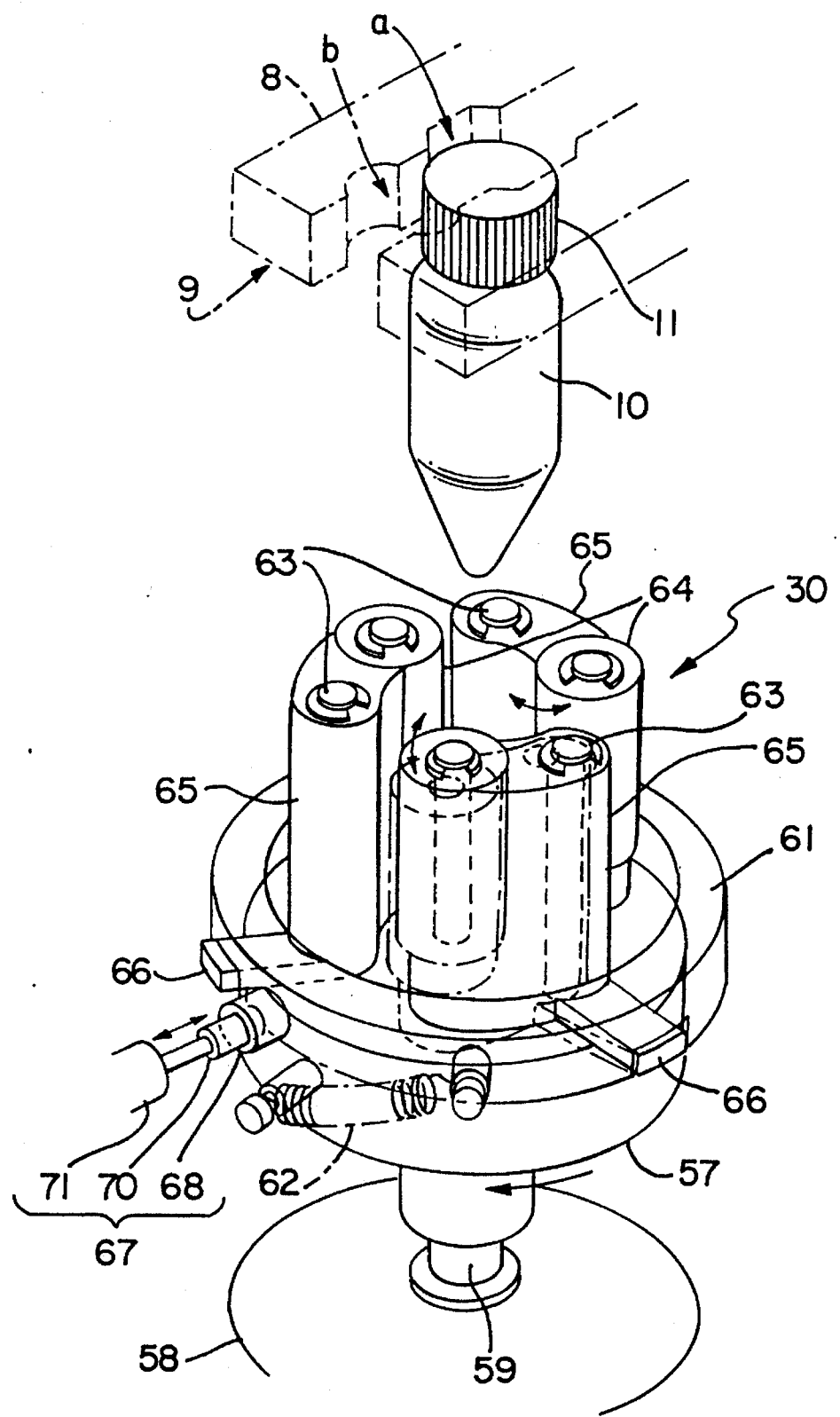
FIG. 14 is a perspective view of the vial sample and a chucking device.

The work hand 9, as seen, for example, in FIG. 14, can have the internal surfaces of its fingers provided with a first concave portion (a) and a second concave portion (b). The first concave portion (a) can be of such a configuration that it will operatively interface with and hold a screw cap 11 that is screwed onto a sample vial 10. The portion (a) can also interface with a cover 13, as shown in FIG. 10, which can be mounted on the reagent storage vials 12. Additionally, as seen in FIG. 4, the concave portion (a) can also grasp a tip holder 15 of the reagent pouring unit 14. The forward concave portion (b) can fasten onto the sample vial 10 and hold it after the screw cap 11 has been removed.

Referring to FIG. 4, the reagent pouring unit 14 includes a pumping member 16 consisting of a cylinder 16a having a relatively small diameter and an interfacing piston 16b that can be reciprocated within the cylinder 16a by a driving means 17, such as an electric motor that can rotate a threaded collar through the rotation of a threaded shaft. The pump can interface with a flexible tube 18 that can be connected to a hollow tip-holding pipe member 20. This tip-holding or receptacle pipe 20 can be removably inserted into a dispensable tip nozzle 19. The tip-holding pipe 20 will frictionally or elastically connect with the tip nozzle 19 and, accordingly, is formed of a hard, rigid material, while the tip holder nozzle 19 can be formed from a disposable medical grade plastic material.

Figure 5:
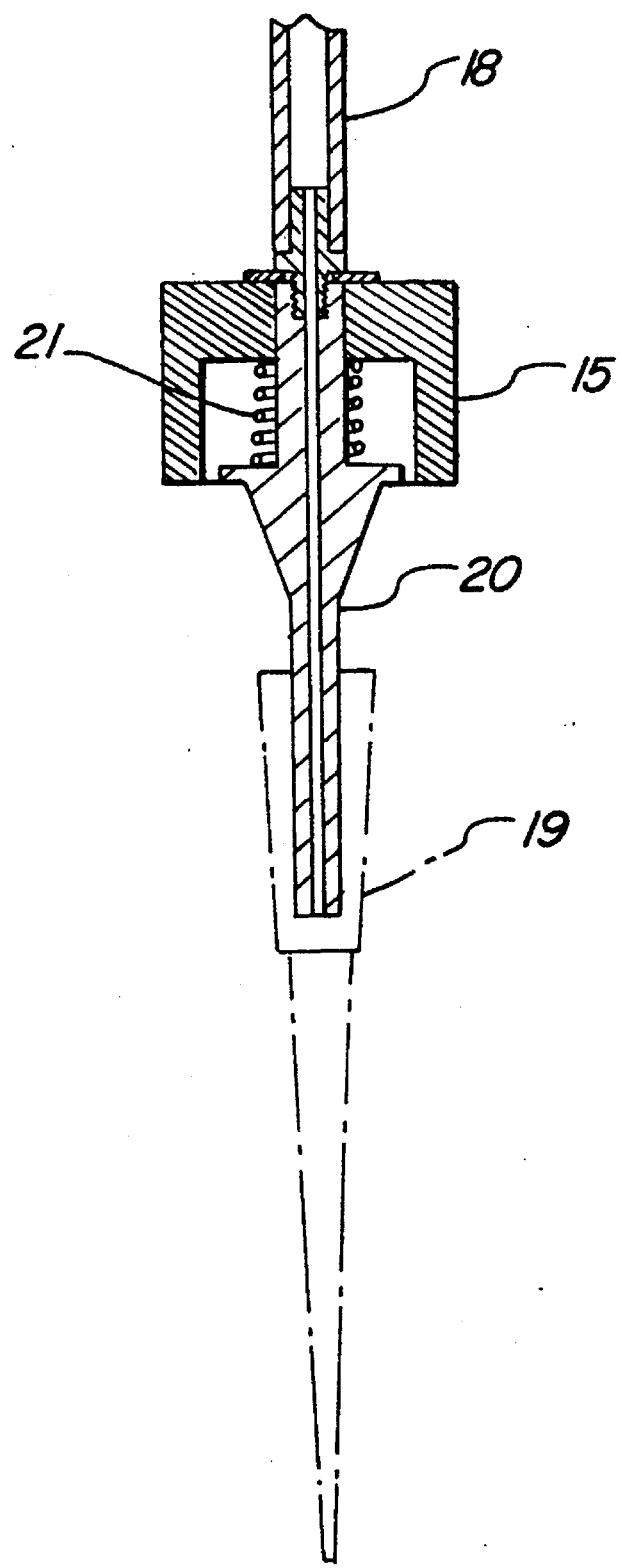
FIG. 5 is a cross-sectional view disclosing a head portion of the dispensing apparatus.

Referring to FIG. 5, a cross-sectional view of the interface of the holder 15, flexible tube 18, and tip-holding pipe 20 is disclosed. The tip-holding pipe 20 is mounted to enable relative movement of the holder 15 by virtue of the helical coil spring 21. The tip holder 15 can interface with the work hand 9. As shown in FIG. 4, the work hand 9 can place the holder 15 in a storage position 36 that can be assigned on the base apparatus 1 in such a position that the flexible tube 18 will not interface with the desired and predetermined movement of the work hand 9 across the base apparatus 1.

Referring to FIGS. 1 and 3, a tip-separating apparatus 22 is provided with a slit (c) adjacent a dispensing shaft that connects with a disposable case 23. The slit (c) has a width or dimension sized to receive the tip-holding pipe 20 which can be inserted therein by the manual hand 9. A tip nozzle 19 has a larger interfacing diameter which can be caught by the undersurface of the slit (c). Thus, when the mechanical hand 9 lifts the holder 15, the tip nozzle 19, which has been used to dispense a reagent solution, is separated from the holding pipe 20 and collected in the case 23.

Referring to FIGS. 1 and 3, a schematic of a storage position 24 for unused nozzle tip 19 is disclosed. A storage casing 25 will be shown in more detail in FIG. 6. Also shown in FIGS. 1 and 3 is a schematic disclosure of the relationship of the vials 12 that contain the reagents to be used in the preanalysis and the storage position 28 of the sample vials 10. In FIG. 3, only a limited number of items are shown stored at each of these stations. It should be appreciated that each of these storage positions will hold a number of items, and that the mechanical hand 9 can access each one of these items.

Between the work stations 26 and 28, table members 27 and 29 are disclosed. Table 27 can hold the covers 13 that are removed from the reagent vials 12. Table 29 is designed to temporarily receive the screw caps 11 that have been removed from the sample vials 10. Adjacent to tables 27 and 29 is a rotatable mounting chuck device 30 that can grasp and releasably hold the body of the sample vial 10 in order to remove the screw cap 11 therefrom. Referring again to FIG. 3, a centrifugal stirrer apparatus 31 is schematically disclosed for rotating a sample vial 10, from which the cap has been removed, and in which liquid reagent has been poured by the pumping apparatus 14. This work station can both weigh and stir the sample and reagent that is in the sample vial 10. The respective work stations 32 and 33 designate heaters for promoting a reaction between the stirred sample and the reagent in the sample vial 10.

Reference number 34 disclosed in FIG. 1 designates an evaporator for distilling away any excess reagent within the sample vial 10 and concentrating the sample within the sample vial 10. As shown in FIG. 3, a washing apparatus 35 is provided for the purged system of the evaporator 34. In addition, a holding storing portion 36 is arranged between the evaporator apparatus 34 and one of the heaters 33.

A discussion of the main constituent members in a reagent reacting device having the above-described construction will now be described.

Figure 6:
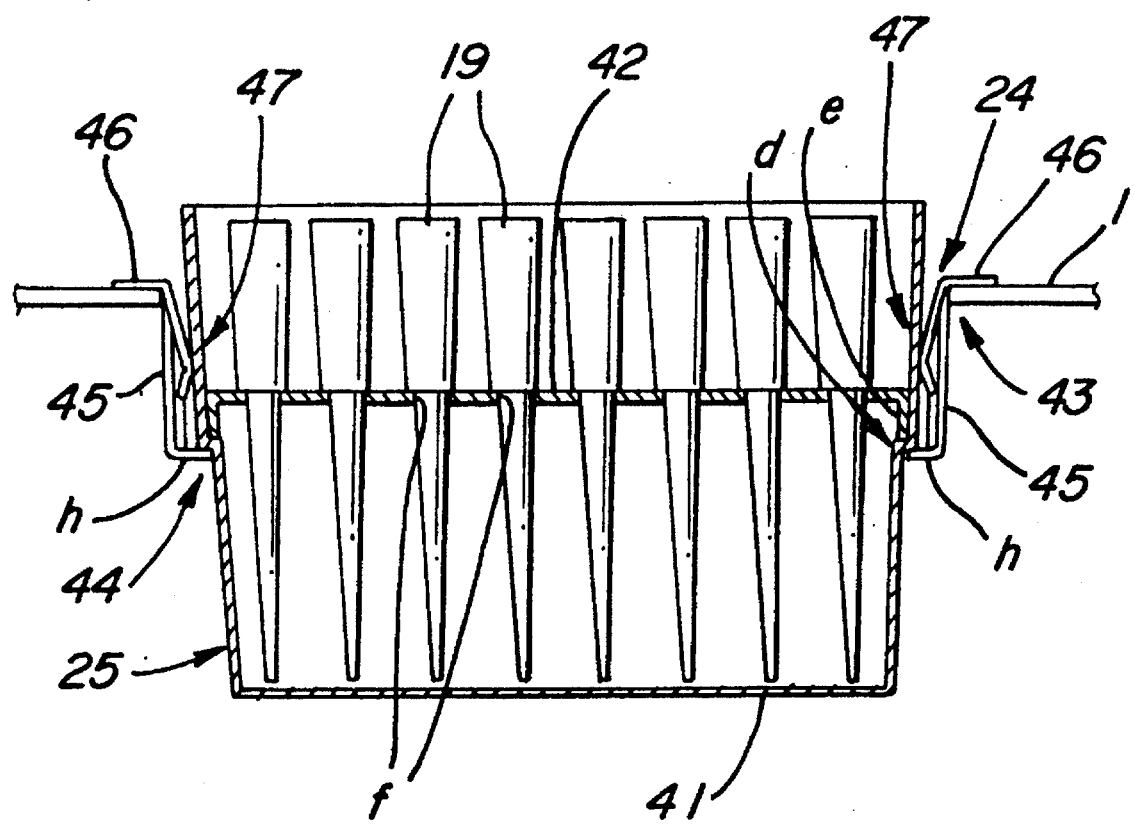
FIG. 6 is a schematic cross-sectional view disclosing a storage case to receive dispenser tip nozzles which can be selectively removed for the pretreatment.
Figure 7:
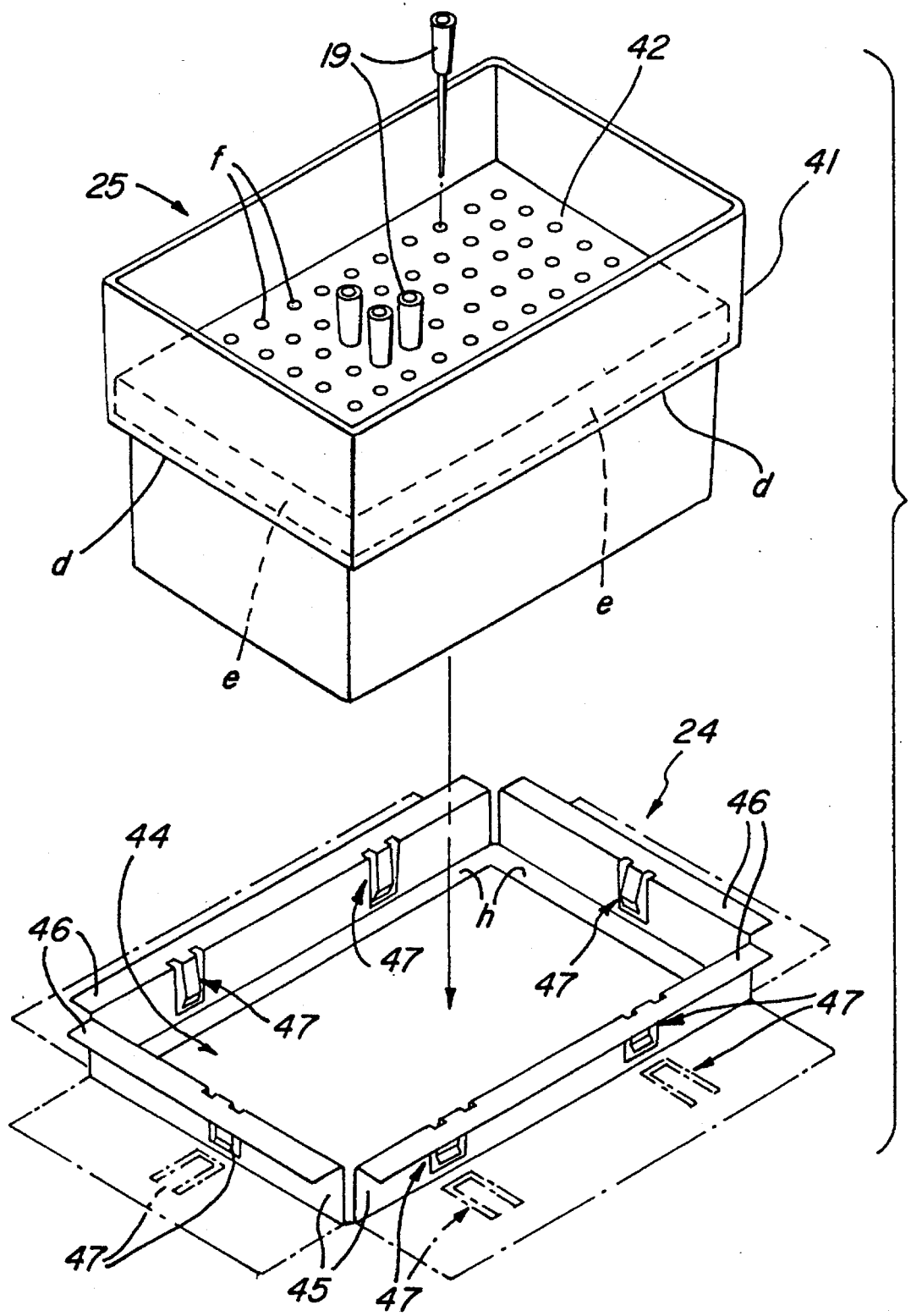
FIG. 7 is a perspective view of the tip nozzle storage case relative to the mounting frame for that work station.

Referring to FIGS. 6 and 7, one embodiment of the tip nozzle storage case 25 is disclosed. This case can have a rectangular configuration and can be formed of a synthetic resin material. As shown in FIG. 7, an outwardly-bent step portion (d) is formed midway between the upper portion and the lower portion of the case body 41. The case body 41 is opened at the upper portion to enable access to the tip nozzles 19. A downwardly-bent piece (e), as shown in FIG. 6, can be supported to closely engage with the expanded portion on the upper portion side of the case body 41. A plate member 42 is supported by the step portion (d) and extends across the entire surface of the case body to form, with the tip-supporting holes (f), support positions for each of the individual tip-dispensing nozzles 19. The holes have a larger diameter than the tip 19 to enable them to be aligned and stored, as shown in FIG. 6. The base 1 has an opening 43 so that a storing portion 24 of the case 25 can be closely engaged. A supporting surface (h) of the step portion (d) is formed around an opening 44 so that a series of holding members 47 are provided for engagement with the storage casing 25. As shown in FIG. 7, one embodiment can have its corners removed, as shown by the dotted chain line. A box-shaped portion, which is elastically engaged with the opening 43 of the base 1, can be formed by bending the sides of the plate material so as to be slightly expanded, whereby the flanges 46 will be formed outwardly to be supported on the upper surface 46 of the base 1. The horizontal standing plate portions 45 can receive U-shaped notches which can be slightly expanded inwardly and bent to form the elastic holding members 47. The fingers 47 can take the configuration shown in FIG. 6 to provide a frictional elastic holding of the upper portion side of the tip nozzle housing case 25. This arrangement also ensures that the relative height of each of the tip nozzles stored within the case member 25 relative to the position of the base 1 of the apparatus will be regulated, to thereby provide an appropriate position for interfacing with the work hand 9 for mounting the tip nozzles 19 on the reagent-dispensing pipe 20. This arrangement further accommodates minor errors in production of the dimensions of the tip nozzle housing casings 25, which are preferably of a relatively inexpensive construction. As a result, the tip nozzles 19 will always be maintained at an appointed height for interfacing with the automatic operation of the work hand 9.

Figure 8B:
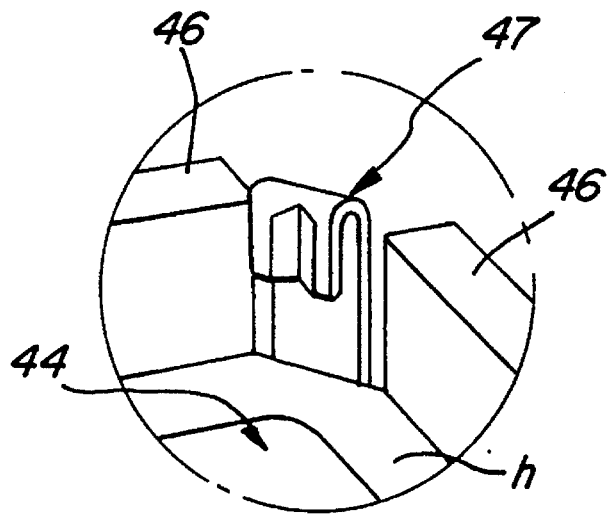
FIGS. 8A and 8B are alternative embodiments of the mounting brackets for interfacing with a storage case of the tip nozzles.
Figure 8A:
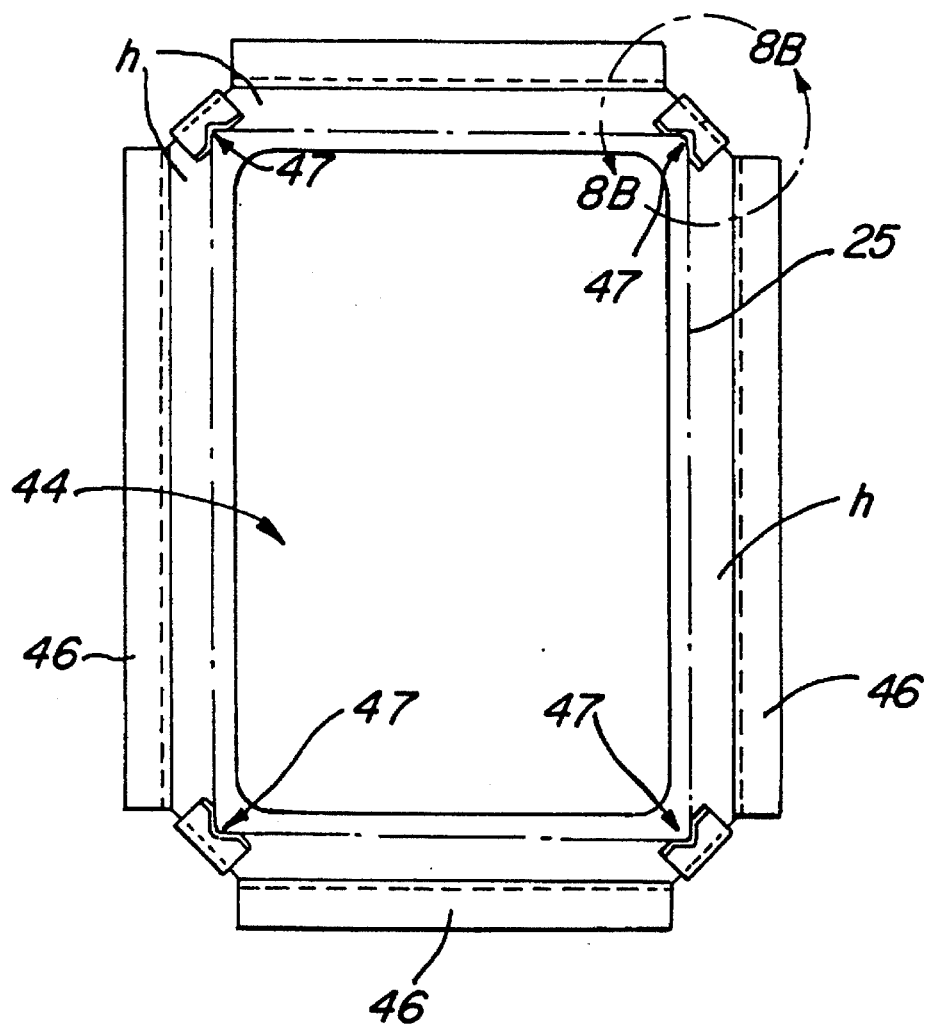

An alternative embodiment of the present invention is disclosed in FIG. 8, wherein a tip-receiving housing case 25 can be modified so that the corner portions are designed to have spring-biased holding members 47', rather than the longitudinal sides as shown in FIG. 7. In this embodiment, the corners can be diagonally based to capture the edges of the storage casing 25 and, while not shown, the adjacent area to each of the corners can also be biased forward on the walls to assist in snugly holding the storage case 25. The storage case 25 has high rigidity in the vicinity of its corner portions and is not easily deformed. As can be appreciated, the elastic holding means 47 that are on the side walls could also be used in combination with this structure.

Figure 9:
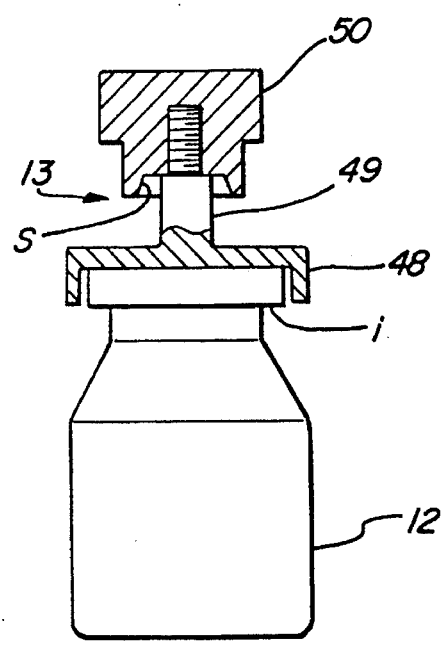
FIG. 9 is a cross-sectional view of a reagent-containing vial and a partial cross-sectional of the vial cover.

Referring to FIG. 9, the reagent containers 12 can have a specially-designed cover 13 comprising a cover body 48, which is sized to extend about the flange portion (i) of the reagent-containing vial 12. The cover 13 has a reduced neck portion 49 that is provided with a tapered portion formed on an upper side thereof and connected with a center of the upper surface of the cover body 48. A step head portion 50 has a diameter smaller than that of the cover body 48, and is screwed onto the tapped portion. A conical surface portion (S) is formed in the lower portion of the head portion 50 in the form of an expanded skirt concave portion, with the axis shaft line of the neck portion 49 as the center.

Figure 12:
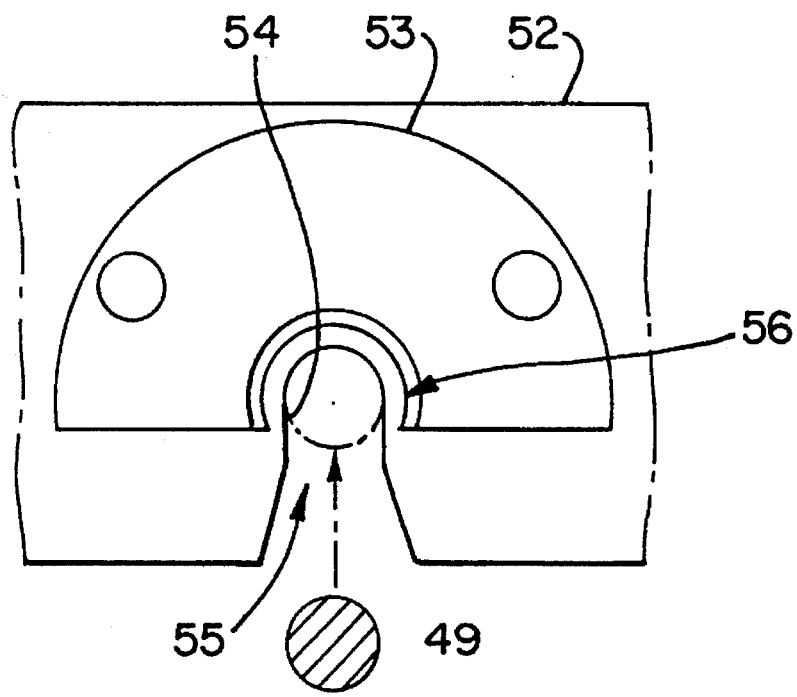
FIG. 12 is a plan view showing the interface of the vial cover with the storage table.
Figure 13:
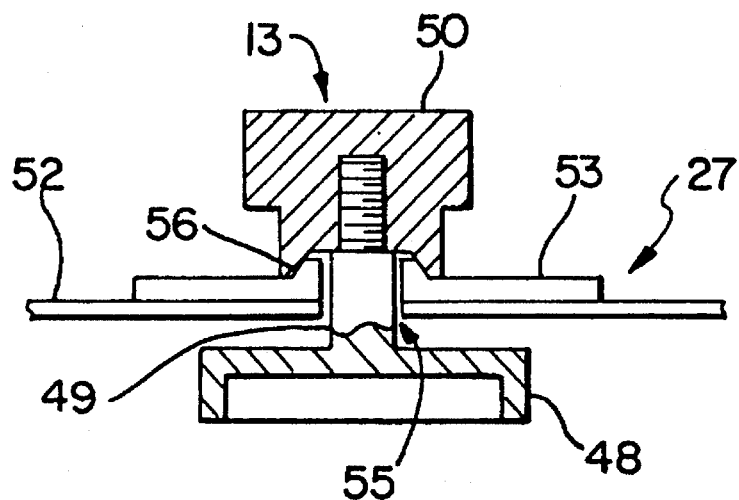
FIG. 13 is a side cross-sectional view showing the relationship of the vial cover with the storage table.

Referring to FIGS. 10–13, the table 27 has a bent plate-like member 52 that is connected with a pin 51 to the base 1 of the apparatus in a cantilevered manner. The plate-like member 52 extends towards the work station 26. Cover-placing members 53 slightly larger than a semicircle configuration can be made of synthetic resins and can be provided on the upper surface of the plate-like member 52 at predetermined intervals along the longitudinal direction. FIG. 12 shows a neck insertion portion 55 which has a diameter slightly larger than the diameter of neck portion 49 of the cover 13. A neck-introducing portion 55 is provided as an entrance into which the neck portion 49 can be inserted into the support table 27 in a horizontal direction by the mechanical hand 9. When the finger members of the mechanical hand 9 release the cover portion 13, it will be appropriately supported by the cover-placing member 53. As is seen in FIG. 13, the cover-placing member 53 has an elevated cover-supporting portion 56 that can both center and mount the sloping surface (S) of the cover 13. The elevated portion 56, as shown, for example, in FIG. 11, assists the mechanical hand 9 in both the engagement and disengagement of the cover member by ensuring an aligned storage portion for the cover member 13. Thus, as shown in FIG. 10, when the mechanical hand 9 grasps the head portion 50, mechanical hand 9 can translate upwardly to release the cover member 13 from the vial body 12. Mechanical hand 9 can then extend across the base apparatus 1 to deposit the cover member 13 in its storage position on its cover-placing member 53. During the releasing phase, the work hand 9 can be moved slightly downward to assist in releasing the head portion 50. The tapered surfaces (S) on the cover member 13 and the conical shape of the cover-supporting portion 56 can ensure an appropriate alignment of the cover member for storage purposes. Such an alignment is important in an automatic operation to provide a reference point to drive the mechanical hand 9 to a select position. Additionally, if there is any vibration in the base apparatus 1, this arrangement prevents any dislocation that can occur as a result of such vibration. When the working hand 9 wishes to retrieve a stored cover member 13 again, it again engages the head portion 50 and slightly raises the head portion to retract it from the storage table 27.

Figure 15:
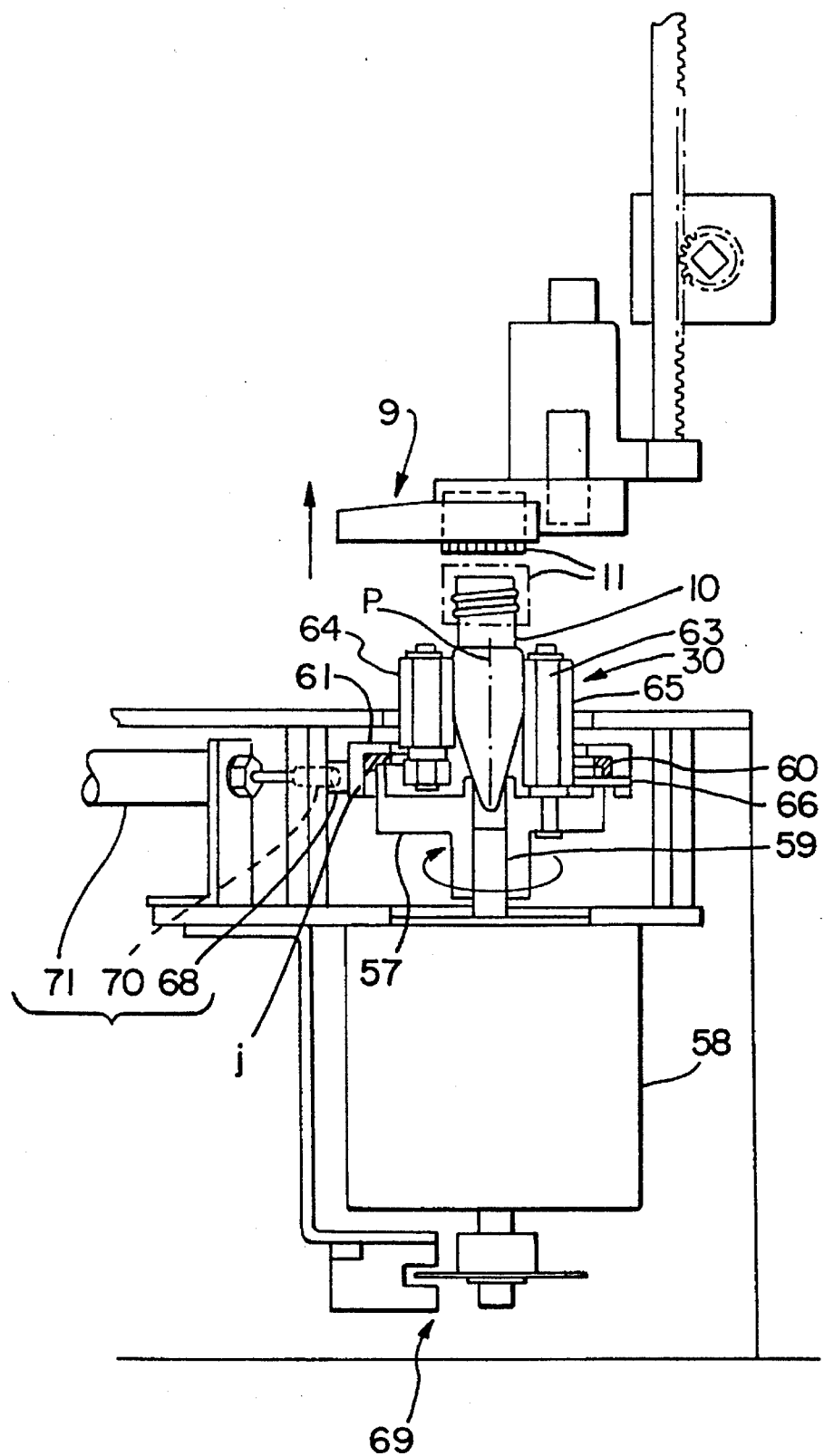
FIG. 15 is an elevated schematic view.
Figure 16:
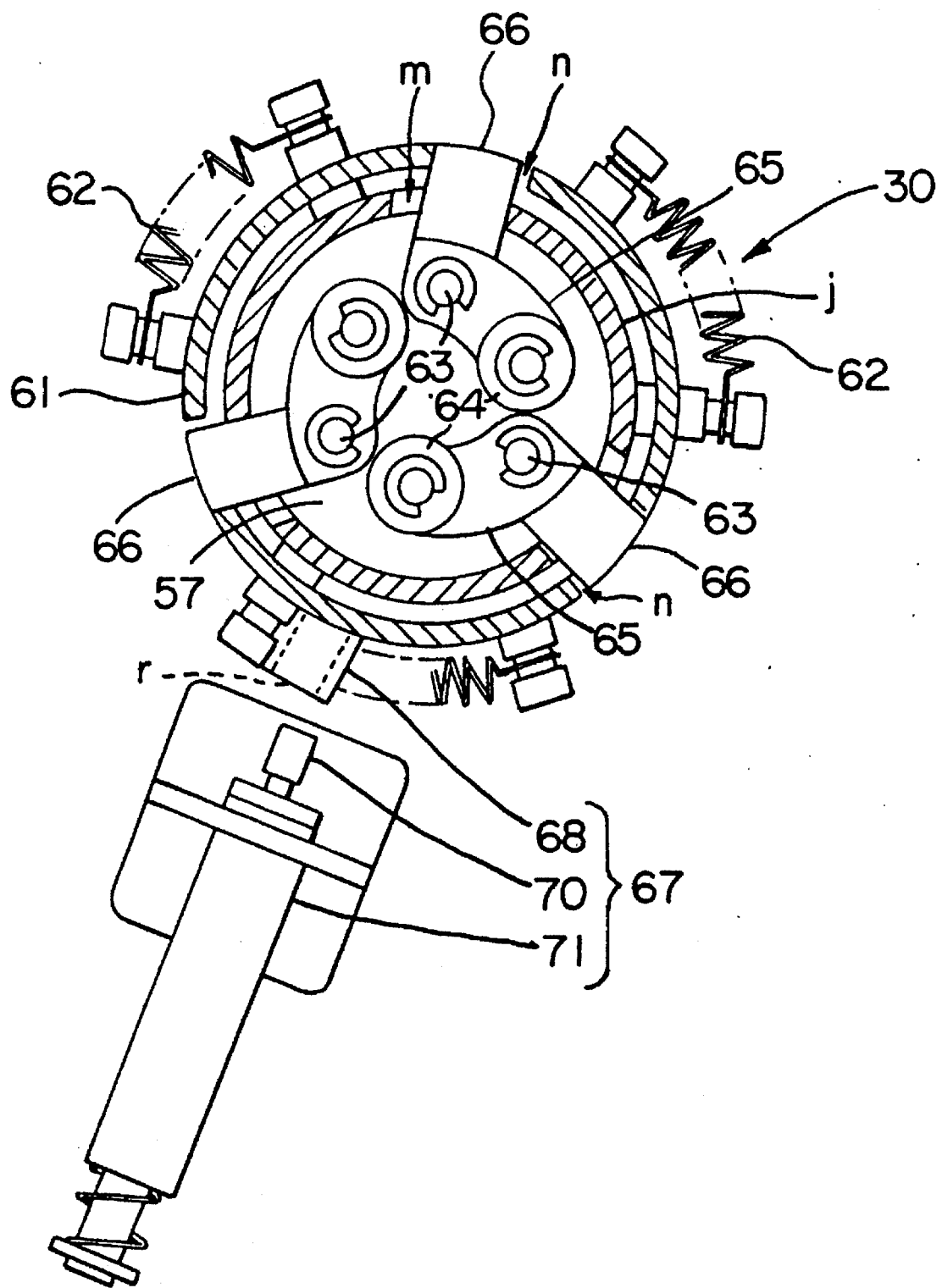
FIG. 16 is a cross-sectional view of the chucking device.

As discussed above, a chucking device 30 was provided between the work stations 26 and 28. Reference can be made to FIGS. 14–16 to see the various elements of the chucking device 30. The chucking device 30 has a disk-like body 57 that is provided with a circumferential wall (j) and is connected to an output shaft 59 of, for example, a stepping motor 58. A ring-like trailing body 61 can be concentrically held on an upper portion of the circumferential wall (j) through a bearing 60. Both the ring-like member 61 and the disk-like body 57 can be relatively rotated and are interconnected with each other through one or more springs 62. The disk-like body 57 is provided, for example, with three support shafts 63 that are regularly placed about the axis of rotation (P). Chucking member 65 is provided with a rubber roller 64 on a side of an idling end thereof, and is supported on, respectively, each of the shafts 63 so as to be symmetrical relative to the center axis (P). The chucking device is designed to permit these rollers to be relatively moved for both opening and grasping the body of the sample vial 10. The bearing 60 between the disk-like body 57 and the ring body 61 that extends over the disk body 57 facilitates easy movement. Engagement members 66 are respectively connected to each of the support shafts 63 and extend through respective openings (m) and (n), seen in FIG. 16, between the respective outer ring body member 61 and the disk body 57. As can be seen, the spring 62 interconnects these two body members together. For example, three springs can be equilaterally positioned to ensure an even application of force. The springs permit relative movement when the disk body 57 is driven by the stepper motor 58. As can be appreciated, when the ring member 61 is fastened or held and the disk body member 57 is driven, there will be a relative rotation against the spring force, and the relative opening edges (m) and (n) will engage the engagement member 66 to relatively displace or pivot the gripping rubber roller 64. This locking means or apparatus 67 is capable of releasably locking the ring member 61 by engagement in a stopper hole (r). Locking apparatus 67 includes a solenoid 71 connected to a stopper member 70 that can be extended and retracted to extend within the stopper hole (r) of the stopper member 70 that can be mounted on the ring member 61. Alternatively, a friction shoe can be used to hold the ring member 61. The provision of the member 68 with the stopper hole (r) ensures a positive engagement.

Figure 17:
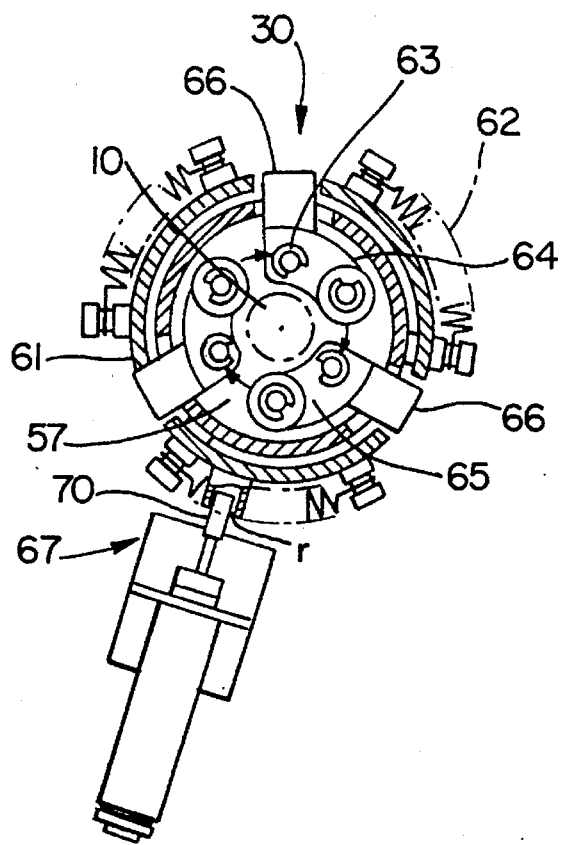
FIG. 17 is another cross-sectional view of the chucking device in an open condition.

When the solenoid 71 is operated with the ring member 61 stopped at the appointed position, the chucking member 65 is in a closed, idling position. The stopper member 70 engages with the stopper hole (r) so as to lock the disk member 61 at the appointed position, as shown in FIG. 16. When the disk body 57 is slightly rotated positively (in a clockwise direction in FIG. 16) against the energizing forces of the spring 62, the idling end of the chucking member 65 is expandedly opened, as shown in FIG. 17. This occurs by slightly rotating the support shaft 63 with the engaging member being engaged with an end portion of the concave portion (n) on the ring member 61.

Figure 18:
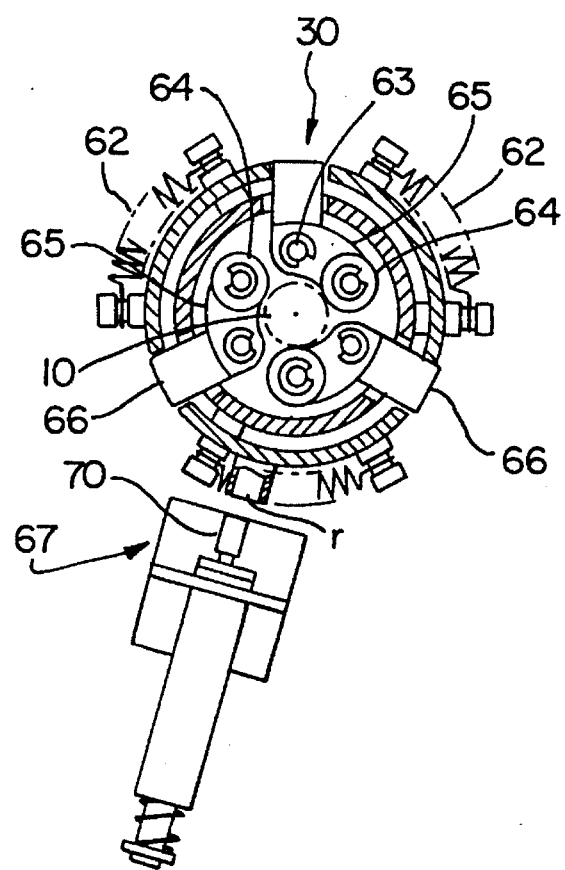
FIG. 18 is a cross-sectional view of the chucking device in a closed position.

A sample vial can then be inserted into the opening of the chucking member 65 having a screw cap 11 (with a right-hand screw construction for convenience). The work hand 9 is grasping the screw cap 11, as shown in FIG. 14. The disk body member 57 can then be reversedly rotated to an original position, and the idling end side of the chucking member 65 closes by the energizing force of the spring 62. Thus, the sample vial 10 will be caught by each of the rubber rollers 64 on the idling end side of the chuck member 65, as seen in FIG. 18. In this position, the screw cap 11 can be automatically removed from the sample vial 10 by reversedly operating the solenoid 71 to release the stopper member 70 from the stopper hole (r). That is, the ring member 61 can now rotate with the disk body 57 with the chucking mechanism 65 securely holding the sample vial 10. The work hand 9 will grasp the screw cap 11. For every rotation of the disk body 57, one pitch of the screw cap 11 will be released until the screw cap 11 can be removed, as shown in FIG. 15.

As can be readily appreciated, the reverse operation permits the screw cap to be screwed onto the sample vial 10, and the sample vial 10 to be removed from the chucking device 30 for subsequent storage purposes. As seen in FIG. 15, an encoder apparatus 69 including, for example, an optical pickup device and an encoding wheel disk, can be used to monitor the movement of the stepper motor 58, as known in this field.

Figure 19:
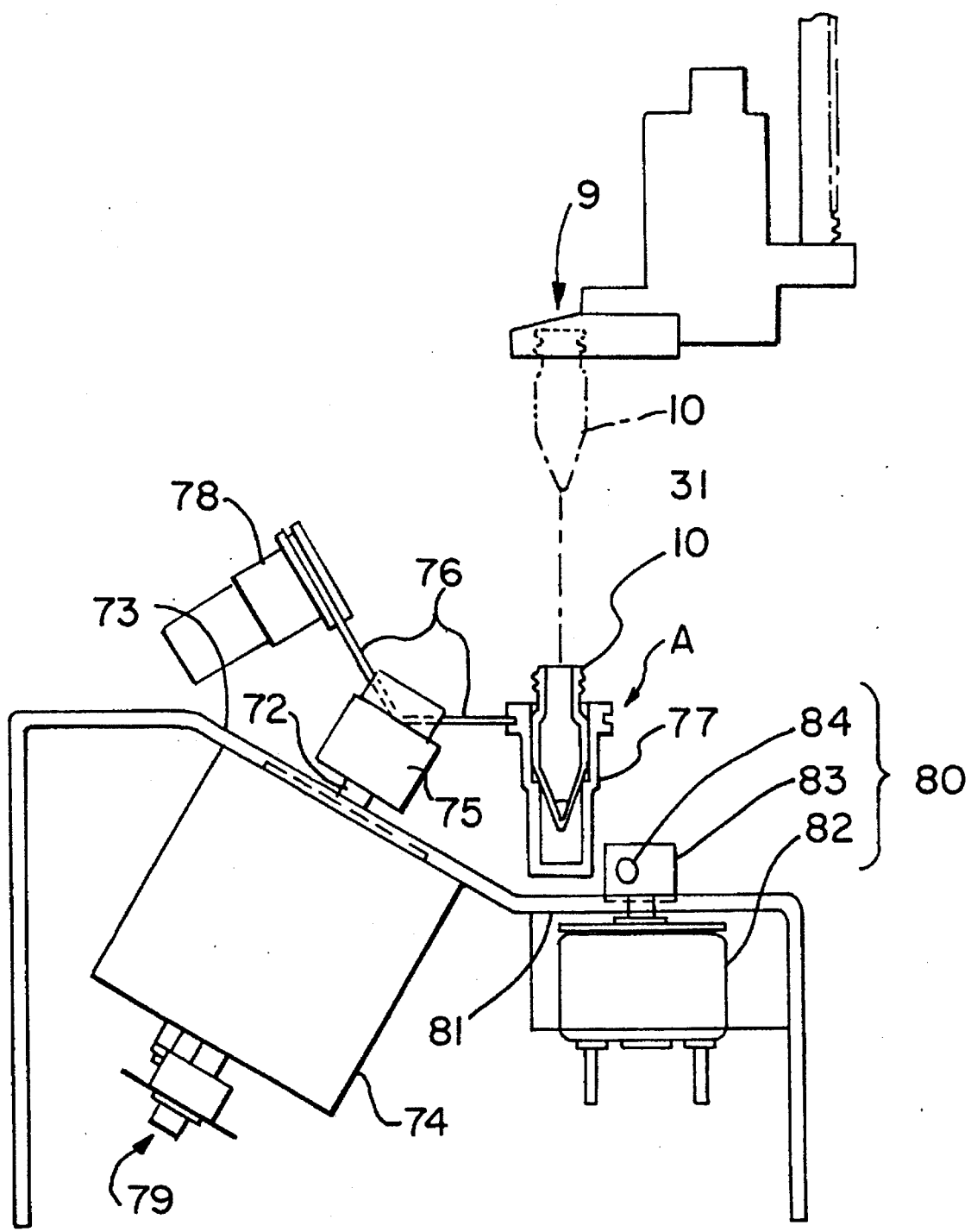
FIG. 19 is a schematic elevated view of the centrifugal stirrer.
Figure 20:
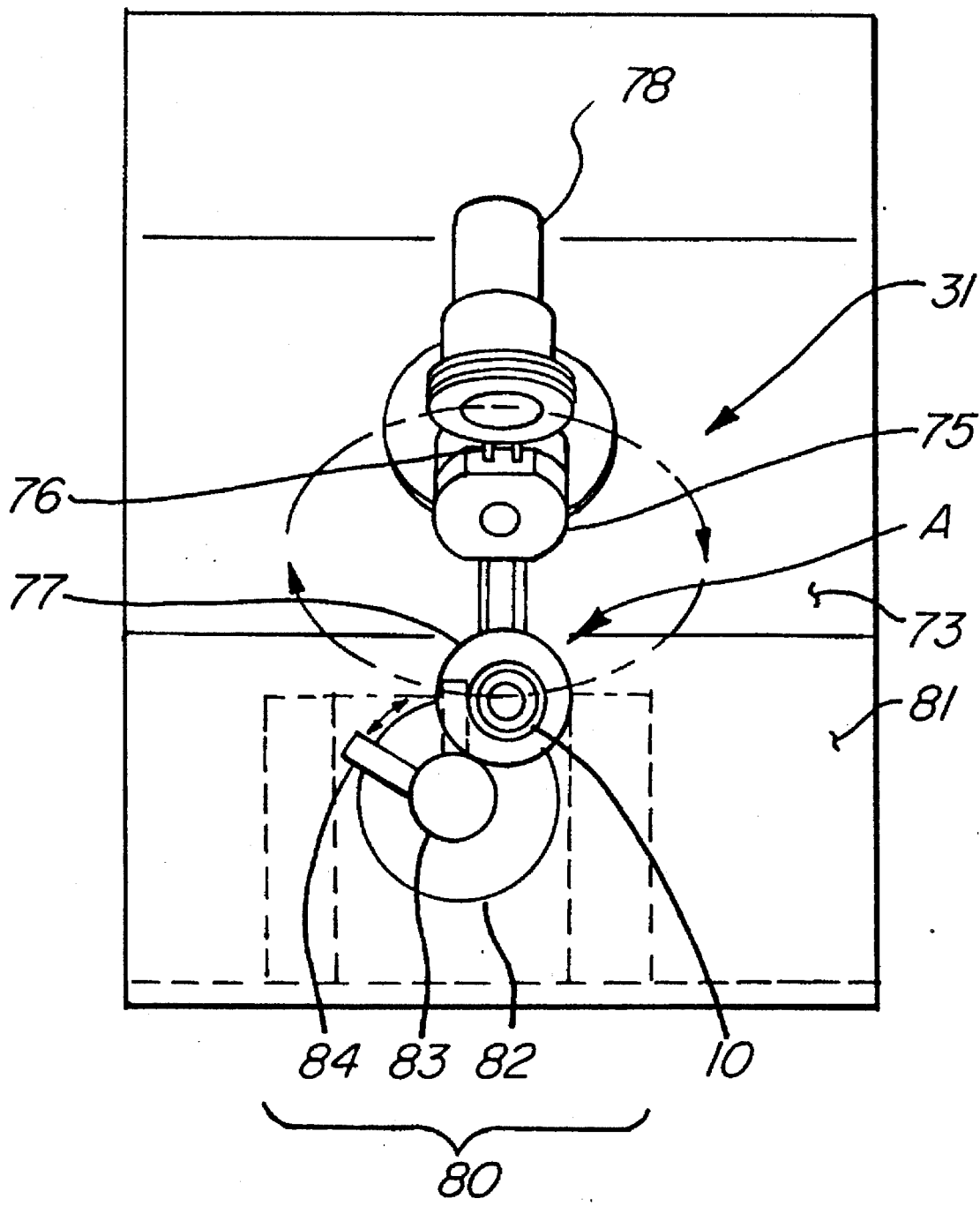
FIG. 20 is a plan view disclosing the relationship of the centrifugal stirrer and the beating device.
Figure 21:
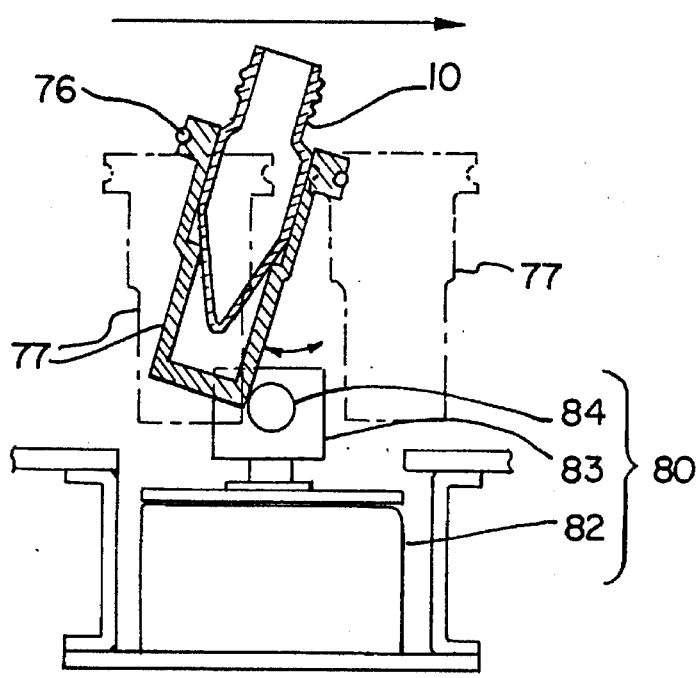
FIG. 21 is an elevated cross-sectional view disclosing a relationship with the bearing device.

Referring again to FIGS. 1, 2, and 3, a centrifugal stirrer apparatus 31 enables the contents of the sample vial 10 to be adequately stirred. This work station of a centrifugal stirrer 31 can be seen in more detail in FIGS. 19–20. A stepping motor 74 is provided on a lower surface side of an inclined mounting plate 73 such that an output shaft 72 extends above the inclined plate 73. A rotatable body 75 is mounted on an axial end of the output shaft 72 and is provided with a pair of elastically flexible arms 76 that can be made, for example, of a spring wire material positioned at predetermined angles and having a phase difference of 180 degrees for balance purposes. One of the pair of flexible arms 76 is provided with a cylindrical vial-receiving member 77, into which the sample vial 10 can be inserted under the condition that a horizontal position is provided to the arms 76 by an appropriate alignment of the centrifugal stirrer 31. In this position, the axis shaft line of the sample vial 10 that is held by the work hand 9 is perpendicular to the opening. The other flexible arm 76 has a weight balance setting dummy body 78 with a weight that is computed to be almost equal to the total weight of the vial-receiving member 77 and the sample vial 10 inserted into the vial-receiving member 77. A position-regulating device 79 can be used for providing an accurate stopping position to the stepping motor 74 so that the vial-receiving member 77 will be at the appropriate position (A) wherein the sample vial 10 can be inserted in a vertical posture.

In addition, a stirring or beating assembly 80 can be provided adjacent the load position of the vial-receiving 77, that is, position (A). This beating assembly 80 includes a rotary solenoid 82 that is provided on a horizontal plate 81, which is further connected with the inclined plate 73. A striking member or hammer boss 83 can be fixedly mounted on an upper end of the axis of rotation of the solenoid 82. A hammer arm 84 can be projected in a lateral direction relative to the boss 83.

Figure 22:
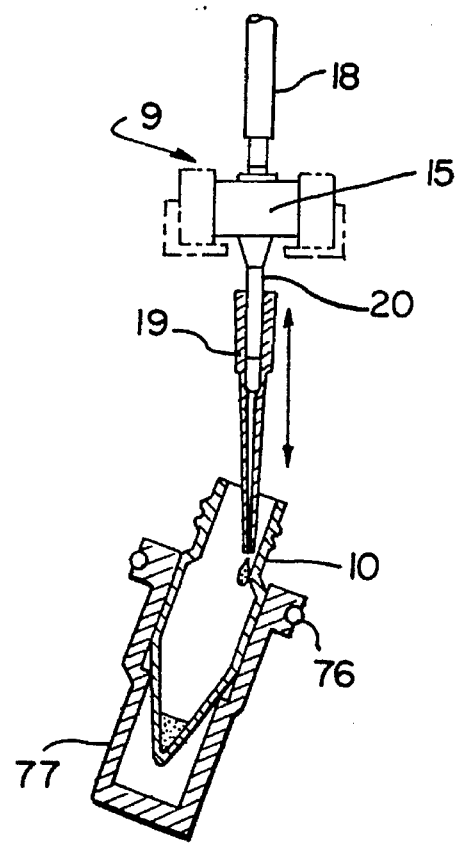
FIG. 22 is a partial cross-sectional elevated view disclosing a relationship of a tip dispenser with a sample vial.

A very small quantity of a reagent can be sucked into a tip nozzle 19 and dispensed into the sample vial 10, as shown in FIG. 22. This can be accomplished advantageously by slightly rotating the stepper motor 74 to slightly move the vial-receiving member 77 at the vial-inserting position (A). This will slightly incline the sample vial 10 that has been inserted into the vial-receiving member 77 to engage a pointed end of the tip nozzle 19 with an inner wall of the sample vial 10, to thereby encourage the dispensing of the reagent liquid.

As can be appreciated, even though a very small amount of liquid reagent may be sucked into the tip nozzle 19, it can still be almost completely poured into the sample vial 10 by operation of the pump 16 of the reagent-pouring unit 14 if the pointed end of the tip nozzle 19 is additionally brought into contact with the inclined wall of the sample vial 10. As a result, the reagent remaining in the pointed end of the tip nozzle 19 can be transferred onto the inner wall of the sample vial 10. This is shown in FIG. 22.

In addition, the reagent can also be poured in the same manner, as shown in FIG. 22, by inserting a tip nozzle 19 into the sample vial 10 when the vial-receiving member 72 is positioned at the vial-inserting position (A), and then slightly rotating the stepping motor 74 to bring the pointed end of the tip nozzle 19 into contact with the inner wall of the vial 10.

When a very small amount of reagent fluid is added to the sample vial, there is a possibility that it may adhere to the inner wall of the sample vial 10 when using the above pouring method. Since it is desired to secure sufficient mixing of the reagent with the sample, the stepping motor 74 can then be rotated at a high speed to provide a centrifugal force to the reagent whereby it will be forcibly integrated into the sample at a bottom portion of the vial. After an appropriate period of time, the stepping motor 74 is rotated at a low speed, and the rotary solenoid 82 is operated to switch over the hammer arm or striker member 84 from an inactive position shown by the full line in FIG. 20 to an active position shown by the dotted line in FIG. 20. In this position, the lower portion side of the vial-receiving member 77 will be impacted by the hammer arm 84 as it is rotated by the centrifugal motor 74. As a result, the sample within the sample vial 10 and the reagent will be effectively vibrated and stirred.

Figure 23:
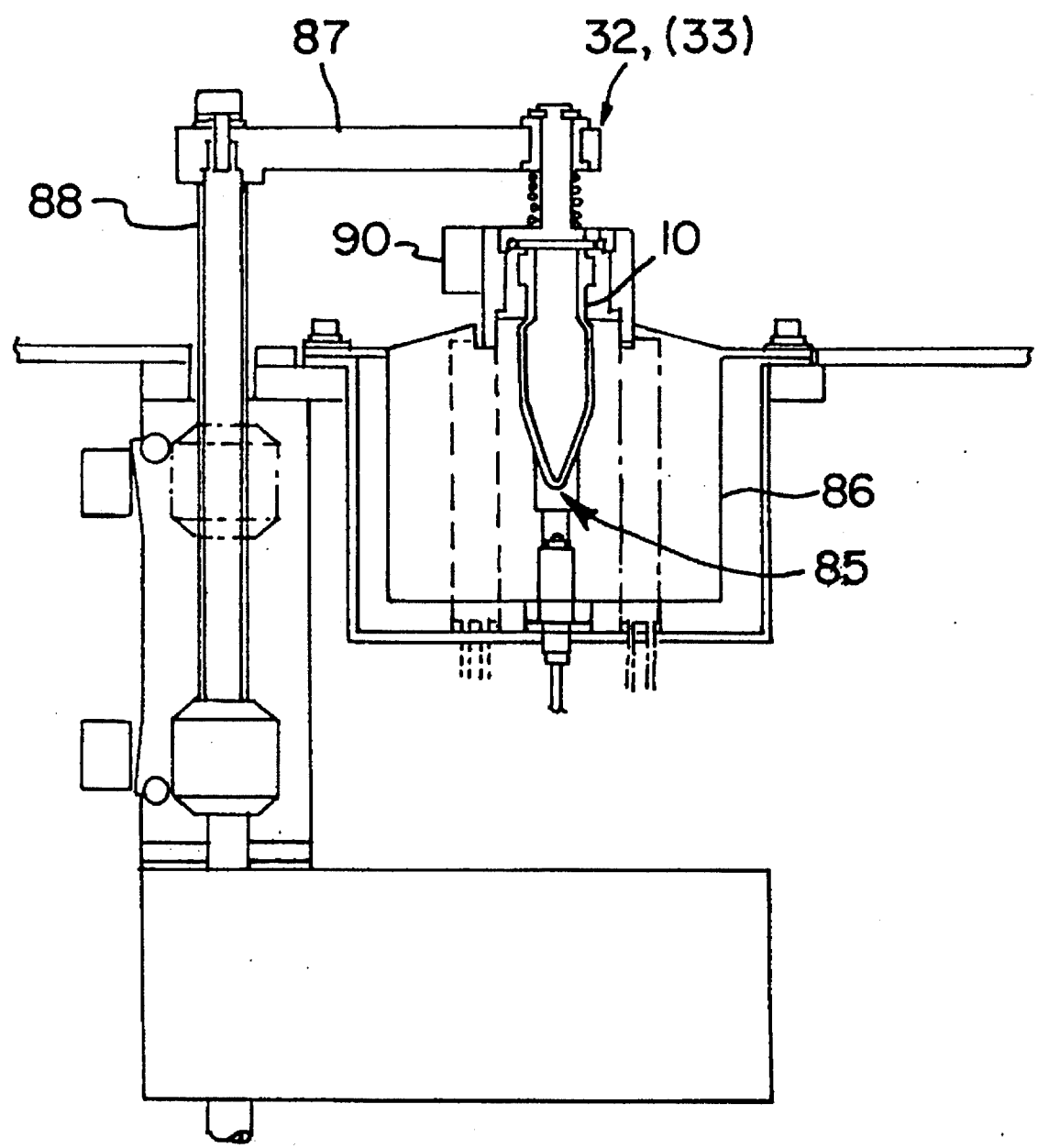
FIG. 23 is an elevated cross-sectional view of the heater.

After completion of this stirring step, the stepping motor 74 can be rotated at a high speed again to force the reagent mixed sample that has been scattered by vibration and stirring to again stick to the inner wall of the vial at the bottom portion of the vial. That is, the sample will again be concentrated at the bottom portion of the vial. The mechanical hand 9 can again retrieve the sample vial 10 when the stepper motor 74 stops the centrifugal motion at position (A). The mechanical hand 9 can take the sample vial to reaction promotion heater assemblies 32 or 33. Each of these heater assemblies have basically the same construction as shown in FIG. 23.

A holding member 88, which can be vertically positioned, includes a rotatable horizontal arm 87. A heat block 86 has a central aperture that forms a holding portion 85 for receiving the sample vial 10. The sample vial 10 can be inserted within the heating block 86 by mechanical arm 9. The horizontal arm 87 can be rotated so that a cover body member 89 can be moved up and down relative to the mouth portion of the sample vial 10. The arm 87 also supports a heater member 90 that is provided with the cover body 89. The cover body 89 can be elastically deformable to seal the surface of the opening mouth of the sample vial 10. Since the reagent-mixed sample within the sample vial 10 is heated by means of the heat block 86, not only is a reaction of the sample in the reagent promoted, but also the reagent-mixed sample can be prevented from being evaporated by means of the cover body 89. In addition, since the cover body 89 is heated by the heater 90, there will be no condensation of the reagent on the cover body 90, and the reagent can be effectively prevented from leaving the sample vial 10.

Figure 24:
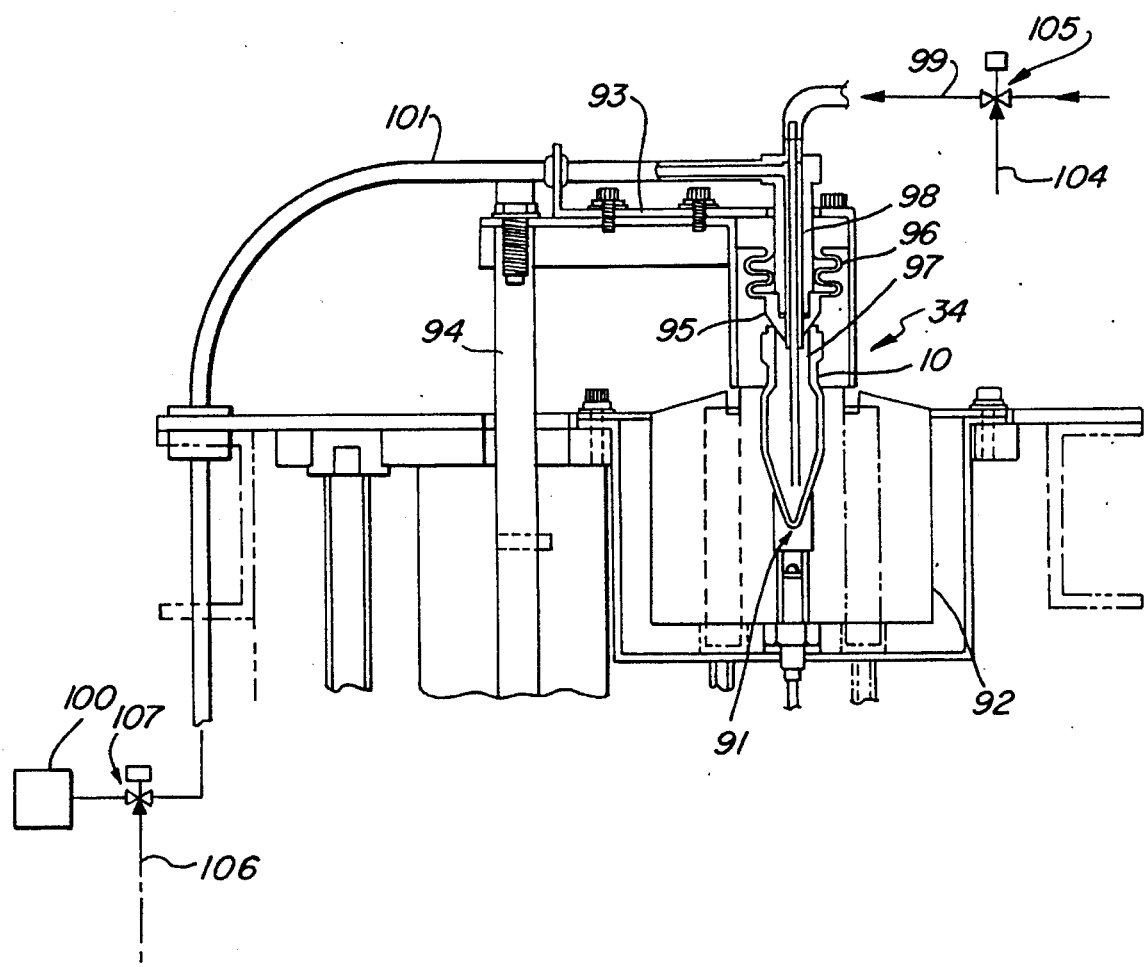
FIG. 24 is an elevated cross-sectional view of the evaporator.

An evaporator work station 34 is shown in FIG. 24 and includes a holding member 94 with a horizontal arm 93 connected to its upper end. The holding member 94 is also capable of being moved up and down and rotated in the vicinity of a heat block 92 that has a holding portion or opening 91 for receiving and retaining the sample vial 10. A cover member 95 is attached to the horizontal arm 93 and can be elastically movable in an up-and-down direction through a bellows member 96, to thereby close the mouth portion of the sample vial 10. A double pair of concentric tubes 97 and 98 are set so that the lower ends thereof may be positioned in the vicinity of a liquid level of the reagent-mixed sample within the sample vial 10. An air supply line 99 can provide a source of air or other gas into the space closed by the cover member 95 of the sample vial 10. Thus, a purging gas can be connected with the upper end of an inner tube 97, while an exhaust line 101 can be connected with a vacuum exhaust means 100 which, in turn, is connected to the upper end of the upper tube 98. A purge gas such as nitrogen can be introduced into the sample vial 10, and subsequently exhausted in a vacuum condition while heating the reagent-mixed sample within the sample vial 10 by means of the heat block 92, to distill off the reagent and like components within the sample vial 10, and thereby concentrate the sample. As can be seen, a valve 105 can control one or more lines of purging gases, while the valve 107 can control the vacuum exhaust means 100. As can be appreciated, these valves can be automatically controlled in correlation with the evaporation process.

A problem that has occurred with evaporator systems is that the reagent is evaporated not only in the sample vial 10 by the heating of the reagent-mixed sample with the heat block 92, but also the reagent-mixed sample can be scattered within the sample vial 10 by the spouting of the purged gas, and mist of the reagent and the regent-mixed sample can be stuck to the outer surface of the inner tube 97 and the inner surface of the exhaust line 101. Thereby contamination between subsequent sample vials can occur, and the exhaust line 101 can actually be restricted or even stopped.

In order to resolve these problems, a washing apparatus 35 is provided in the vicinity of the evaporator 34.

Figure 25:
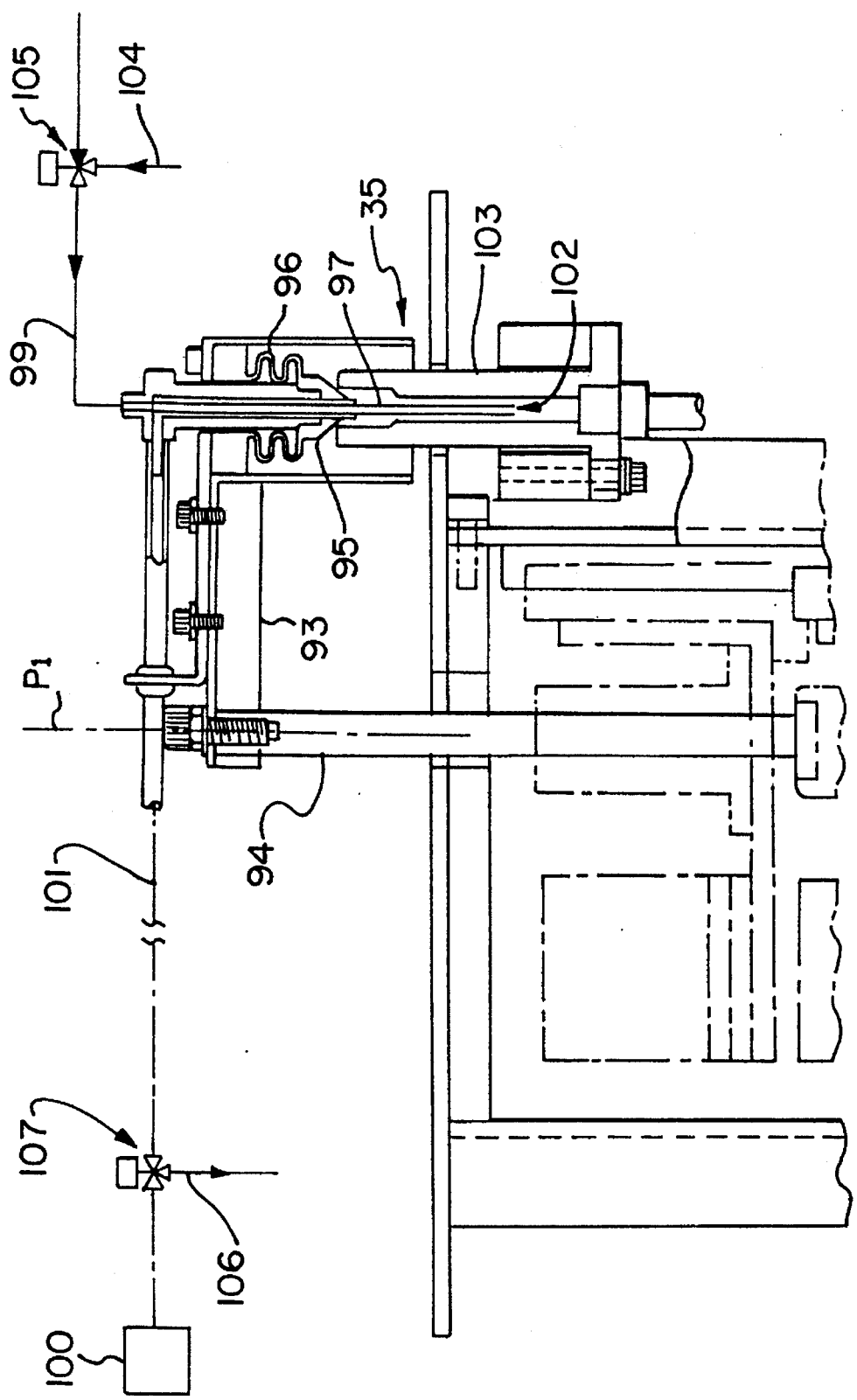
FIG. 25 is an elevated cross-sectional view of the washing station for the purged gas system of the evaporator.

Reference can be made to FIG. 25 to disclose the washing device 35 of the present invention. The arm holding member 94 is constructed so that it is rotatably movable about the longitudinal axis shaft line ($P_1$), as shown in FIG. 3. A washing block 103 is provided with a washing chamber 102, with an open portion thereof being arranged at a position where it can also be closed by the cover member 95. In this arrangement, the inner tube 97 is inserted through the washing chamber 102, and the three-way valve 105 is provided with a washing liquid supply line 104 connected therewith midway between the purge gas supply line 99 in order to be switched, to thereby supply the washing chamber 102 with a washing liquid instead of the purging gas. Additionally, a three-way valve 107 is provided with a waste liquid line 106, whereby the washing liquid can be exhausted from the exhaust line 101. The washing liquid can then be utilized to thoroughly cleanse the cover member 95 and both the gas supply line 99 and exhaust line 101, along with the concentric pipes 96 and 98. Therefore, any reagent-mixed sample that is stuck to the outer surface of the inner tube 97 or the inner surface of the exhaust line 101 can be forcibly washed away. Thus, contamination between sample vials and stoppage of the exhaust line 101 can be prevented. As can be appreciated, purge gas can be used to further force the washing liquid to the discharge line prior to a subsequent evaporation procedure.

As an illustration of the operation of the present apparatus, the following process steps are performed automatically by the present apparatus:

1. The sample vial 10 is supplied to the chucking device 30 from the container-holding portion 28 by means of the work hand 9.

2. The screw cap 11 is removed by rotating the chucking device 30 under the condition that the screw cap 11 is held firmly by means of the work hand 9.

3. The removed cap 11 is transferred onto the table 29 for temporarily storing the screw cap 11.

4. The sample vial 10, from which the cap 11 has been removed, is then moved to the centrifugal stirrer 31.

5. The vial cover 13 is removed from the reagent vial 12, in which a first reagent, for example, pyridylamination, is housed, by means of the work hand 9, and the removed vial cover 13 is transferred onto the table 27 for temporary storage.

6. The tip holder 15 is removed from the holder-storing portion 36 by means of the work hand 9 and the tip nozzle 19 is engagedly held in the tip-holding pipe 20.

7. An appointed quantity of the first reagent (10 µl of a solution of 2-aminopyridine in acetic acid) is sucked from the reagent vial 12 by means of the tip nozzle 19, and the first reagent is poured into the sample vial 10 as it is held in the centrifugal stirrer 31.

8. The tip nozzle 19, which has been used, is discharged into the case 23 by means of the tip-separating means 22.

9. The tip holder 15 is stored in the holder-storing portion 36.

10. The vial cover 13 for the reagent vial 12, in which the first reagent is housed, is closed.

11. The first reagent within the sample vial 10 is weighed by means of the centrifugal stirrer 31 (the reagent stuck to the wall surface of the sample vial is collected on the bottom portion of the vial by the centrifugal force, for example, by stirring for about 20 seconds).

12. The sample and the first reagent are stirred by means of the hammer arm 84 under the condition that the sample vial 10 is rotated at low speed after the above-described weighing and the reagent-mixed sample, which has been stirred, is weighed (about 40 seconds).

13. The sample vial 10 is moved to the heater 32 by means of the work hand 9.

14. A thermal reaction for the pyridylamination between the sample and the first reagent is conducted for about 20 minutes at a temperature of, for example, about 90° C. in the heater 32.

15. After the reaction, the sample vial 10 is transferred to the evaporator 34.

16. In the evaporator 34, the first reagent is distilled off (the evaporation is continued for 20 minutes at a temperature of 60° C. while supplying the sample vial 10 with an inert gas, such as an $N_2$ gas, and suctioning gases within the vial 10 in a vacuum).

17. The sample vial 10 is transferred to the centrifugal stirrer 31.

In the following steps 18 to 27, the reductive process is conducted by the same cycle as in the above steps 5 to 14:

18. The cover 13 of the reagent vial 12, in which a second reagent for the reduction is housed, is removed and the removed cover 13 is transferred onto the table 27.

19. The tip holder 15 is taken out and the tip nozzle 19 is engagedly held by means of the work hand 9.

20. An appointed quantity of the second reagent (10 µl of a solution of boron dimethyl amine in acetic acid) is sucked and the second reagent is poured into the sample vial 10.

21. The tip nozzle 19, which has been used, is discharged into the case 23.

22. The tip holder 15 is stored in the holder-storing portion 36.

23. The vial cover 13 for the reagent vial 12, in which the second reagent is housed, is closed.

24. The second reagent is weighed (about 20 seconds).

25. The sample and the second reagent are stirred by means of the hammer arm 84 and the reagent-mixed sample, which has been stirred, is weighed (about 40 seconds).

26. The sample vial 10 is moved to the heater 33.

27. The thermal reaction for the reduction is conducted for 20 minutes at a temperature of, for example, about 90° C. in the heater 33.

28. subsequently, the sample vial 10 is transferred into the centrifugal stirrer 31.

In the following steps 29 to 36 and 37 to 44, the first azeotropic process and the second azeotropic process are conducted by the same cycle as in the above steps 18 to 25:

29. The cover 13 of the reagent vial 12, in which the third reagent for the first azeotropic process is housed, is removed and the removed cover 13 is transferred onto the table 27.

30. The tip holder 15 is taken out and the tip nozzle 19 is engagedly held by means of the work hand 9.

31. The appointed quantity of the third reagent (20 μl of methanol) is sucked and the third reagent is dividedly poured into the sample vial 10.

32. The tip nozzle 19, which has been used, is abandoned into the case 23.

33. The tip holder 15 is stored in the holder-storing portion 36.

34. The vial cover 13 for the reagant vial 12, in which the third reagent is housed, is closed.

35. The third reagent is weighed (about 20 seconds).

36. The sample and the third reagent are stirred by means of the hammer arm 84 and the reagent-mixed sample, which has been stirred, is weighed (about 40 seconds).

37. The cover 13 of the reagant vial 12, in which the fourth reagent for the second azeotropic process is housed, is removed and the removed cover 13 is transferred onto the table 27.

38. The tip holder 15 is taken out and the tip nozzle 19 is engagedly held by means of the work hand 9.

39. The appointed quantity of the fourth reagent (40 μl of toluene) is sucked and the fourth reagent is dividedly poured into the sample vial 10.

40. The tip nozzle 19, which has been used, is discharged into the case 23.

41. The tip holder 15 is stored in the holder-storing portion 36.

42. The vial cover 13 for the reagant vial 12, in which the fourth reagent is housed, is closed.

43. The fourth reagent is weighed (about 20 seconds).

44. The sample and the fourth reagent are stirred by means of the hammer arm 84 and the reagent-mixed sample, which has been stirred, is weighed (about 40 seconds).

Then, the same cycle is taken as in the above-described steps 15 to 17:

45. After the reaction, the sample vial 10 is transferred to the evaporator 34.

46. In the evaporator 34, the third and fourth reagents are distilled off (the evaporation is continued for 10 minutes at a temperature of 60° C. while supplying the sample vial 10 with an inert gas, such as an $N_2$ gas, and suctioning gases within the vial 10 in a vacuum).

47. The sample vial 10 is transferred to the centrifugal stirrer 31.

In the following steps 48 to 55 and 56 to 63, the third azeotropic process and the fourth azeotropic process by the same cycle as in the above steps 37 to 44:

48. The cover 13 of the reagent vial 12, in which the fifth reagent for the third azeotropic process is housed, is removed and the removed cover 13 is transferred onto the table 27.

49. The tip holder 25 is taken out and the tip nozzle 19 is engagedly held by means of the work hand 9.

50. The appointed quantity of the fifth reagent (20 μl of methanol) is sucked and the fifth reagent is poured into the sample vial 10.

51. The tip nozzle 19, which has been used, is discharged into the case 23.

52. The tip holder 15 is stored in the holder-storing portion 36.

53. The vial cover 13 for the reagent vial 12, in which the fifth reagent is housed, is closed.

54. The fifth reagent is weighed (about 20 seconds).

55. The sample and the fifth reagent are stirred by means of the hammer arm 84, and the reagent-mixed sample, which has been stirred, is weighed (about 40 seconds).

56. The cover 13 of the reagent vial 12, in which the sixth reagent for the fourth azeotropic process is housed, is removed and the removed cover 13 is transferred onto the table 27.

57. The tip holder 15 is taken out and the tip nozzle 19 is engagedly held by means of the work hand 9.

58. An appointed quantity of the sixth reagent (40 μl of toluene) is sucked and the sixth reagent is poured into the sample vial 10.

59. The tip nozzle 19, which has been used, is abandoned into the case 23.

60. The tip holder 15 is stored in the holder-storing portion 36.

61. The vial cover 13 for the reagent vial 12, in which the sixth reagent is housed, is closed.

62. The sixth reagent is weighed (about 20 seconds).

63. The sample and the sixth reagent are stirred by means of the hammer arm 84 and the reagent-mixed sample, which has been stirred, is weighed (about 40 seconds).

Then, the same cycle is taken as in the above-described steps 45 to 47:

64. After the reaction, the sample vial 10 is transferred to the evaporator 34.

65. In the evaporator 34, the fifth and sixth reagents are distilled off (the evaporation is continued for 10 minutes at a temperature of 60° C. by supplying the sample vial 10 with an inert gas, such as an $N_2$ gas, and suctioning gases within the vial 10 in a vacuum).

66. The sample vial 10 is transferred into the centrifugal stirrer 31.

In the following steps 67 to 74, the fifth azeotropic process is conducted by the same cycle as in the above steps 56 to 63:

67. The cover 13 of the reagent vial 12, in which the seventh reagent for the fifth azeotropic process is housed, is removed and the removed cover 13 is transferred onto the table 27.

68. The tip holder 15 is taken out and the tip nozzle 19 is engagedly held by means of the work hand 9.

69. The appointed quantity of the seventh reagent (40 μl of toluene) is sucked and the seventh reagent is poured into the sample vial 10.

70. The tip nozzle 19, which has been used, is discharged into the case 23.

71. The tip holder 15 is stored in the holder-storing portion 36.

72. The vial cover 13 for the reagent vial 12, in which the seventh reagent is housed, is closed.

73. The seventh reagent is weighed (about 20 seconds).

74. The sample and the seventh reagent are stirred by means of the hammer arm 84 and the reagent-mixed sample, which has been stirred, is weighed (about 40 seconds).

Then, the same cycle is taken as in the above-described steps 64 and 65:

75. After the reaction, the sample vial 10 is transferred to the evaporator 34.

76. In the evaporator 34, the seventh reagent is distilled off (the evaporation is continued for 10 minutes at a temperature of 60° C. by supplying the sample vial 10 with an inert gas, such as an $N_2$ gas, and suctioning gases within the vial 10 in a vacuum).

Thus, the pyridylamination, the reduction, and the first to fifth azeotropic processes are over, and then:

77. The sample vial 10 is transferred to the chucking device 30.

78. The purge gas system of the evaporator 34 is washed simultaneously with the above-described transfer of the sample vial 10.

When the final evaporation of the sample is finished, the arm holding member is rotated and the washing chamber 102 of the washing block 103 is closed with the cover member 95, while the three-way valves 105 and 107 are switched over to a washing liquid supplying mode of operation to wash any mist and the like of the reagents by the use of the purged gas supplied line 99 and the purged gas exhaust line 101.

79. The cap 11 was held on the table 29 for temporarily storing the cap 11 and it is now transferred to the chucking device 30 by means of the work hand 9.

80. The chucking device 30 is rotated under the condition that the cap 11 is held to close the sample vial 10 with the screw cap 11.

81. The cap-provided vial 10 is transferred to the sample vial-holding portion 28.

Accordingly, the pretreatment of the sample prior to an analysis for the content of sugar and molecular change is finished. As can be appreciated from the above description, the automation of the pretreatment apparatus enables various types of operation in the pretreatment, such as the mounting and removal of the caps on and from the mouth portion of the sample vial and the reagent vials, along with the replacement of the nozzle tip, to be accomplished automatically. Various kinds of reagents can be automatically poured into the sample vial. The sample vial can be automatically transferred for various heating, stirring, and evaporation procedures.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. In an automatic system for treatment of samples in a vial with reagents, the improvement comprising:

means for introducing a sample vial having a sealing member;

means for automatically removing the sealing member and storing the sealing member for future operative retrieval and use, including a plurality of parallel support shafts circumferentially positioned; a plurality of gripping members, each member being mounted to one of said support shafts; and means for concentrically translating said plurality of support shafts in parallel alignment radially inward, such that said sample vial received within said circumferentially-arranged plurality of gripping members is gripped thereby;

means for dispensing a reagent, including a conduit member, into the sample vial;

means for storing a reagent vial having a closure member;

means for automatically removing the closure member and storing the closure member for future operative retrieval and use, including a storing table with peripheral storing stations;

a source of dispensing nozzle tips;

means for selecting a dispensing nozzle tip and mounting it on the conduit member;

means for inserting the nozzle tip into an opened reagent vial and withdrawing the reagent into the nozzle tip, whereby the means for dispensing causes the nozzle tip to contact an inner wall of the sample vial to ensure a complete discharge of the reagent; and means for discharging the nozzle tip after it has dispensed reagent into the sample vial.

2. The invention of claim 1 wherein the means for selecting and mounting a dispensing nozzle tip includes a holder, a spring mounted in the holder and a tip holding a pipe member that is biased by the spring.

3. The invention of claim 1 wherein the means for discharging the nozzle tip includes a tip separating apparatus having a slit dimensioned for receiving the nozzle tip and securing the same for release from the conduit member.

4. The automatic system of claim 1 wherein said plurality of gripping members comprises a plurality of gripping rollers rotatably mounted to said plurality of support shafts.

5. The automatic system of claim 1 further comprising means for removing the sealing member while said sample vial is secured by said plurality of gripping members.

6. The automatic system of claim 5 wherein said removing means further comprises means for monitoring a position of said sealing member relative to said sample vial, the monitor means determining when removal of said sealing number is completed.

7. The invention of claim 1 further including means for heating a mixture of reagent and sample, including a cover member that is heated to minimize condensation.

8. The invention of claim 7 wherein the cover member is elastically deformable to seal the sample vial.

9. The invention of claim 7 further including means for introducing and removing a washing liquid to the cover member.

10. In an automatic system for treatment of samples in a vial with reagents, the improvement comprising:

means for introducing a sample vial having a sealing member;

means for automatically removing the sealing member and storing the sealing member for future operative retrieval and use;

means for dispensing a reagent into the sample vial; and means for automatically stirring the sample and reagent in the sample vial, including a rotatable body provided with at least one elastically flexible arm, a vial receiving member connected to the arm for rotation, and a rotary solenoid member having a hammer arm that can be selectively inserted in a path of movement of the vial receiving member to agitate the sample vial.

11. The invention of claim 10 wherein the means for automatically removing the sealing member includes a plurality of parallel support shafts circumferentially positioned; a plurality of gripping members, each member being mounted to one of said support shafts; and means for concentrically translating said plurality of support shafts, such that said sample vial when received within said circumferentially-arranged plurality of gripping members is gripped thereby.

12. In an automatic system for treatment of samples in a vial with reagents, the improvement comprising:

means for introducing a sample vial having a sealing member; and means for automatically removing the sealing member and storing the sealing member for future operative retrieval and use, including a plurality of parallel support shafts circumferentially positioned; a plurality of gripping members, each member being mounted to one of said support shafts; and means for concentrically translating said plurality of support shafts in parallel alignment radially inward, such that said sample vial received within said circumferentially-arranged plurality of gripping members is gripped thereby.

13. The invention of claim 12, further including means for dispensing a reagent into the sample vial means for centrifuging the sample vial with the sample and reagent and means for selectively impacting the sample vial to stir the sample and reagent.

* * * * *